(12) United States Patent
Tae et al.

(10) Patent No.: US 7,816,498 B2
(45) Date of Patent: Oct. 19, 2010

(54) MONOCLONAL ANTIBODY FOR HIPPURIC ACID ANTIGEN

(75) Inventors: Gun Sik Tae, #209-908 Sinbanpohansin Apt., Jamwon-dong, Seocho-gu, Seoul 137-030 (KR); Hee Sun Chung, Seoul (KR); Oh Hyep Kwon, Suwon-si (KR); Seung Hwa Lee, Siheung-si (KR)

(73) Assignees: HBI Co., Ltd., Anyang-si (KR); Gun Sik Tae, Seoul (KR)

( * ) Notice: Subject to any disclaimer, the term of this patent is extended or adjusted under 35 U.S.C. 154(b) by 1 day.

(21) Appl. No.: 11/989,066

(22) PCT Filed: Jul. 30, 2005

(86) PCT No.: PCT/KR2005/002493
§ 371 (c)(1),
(2), (4) Date: May 8, 2008

(87) PCT Pub. No.: WO2007/011091
PCT Pub. Date: Jan. 25, 2007

(65) Prior Publication Data
US 2009/0227777 A1  Sep. 10, 2009

(30) Foreign Application Priority Data
Jul. 22, 2005  (KR) ...................... 10-2005-0067033

(51) Int. Cl.
C07K 16/00  (2006.01)
C07K 16/18  (2006.01)
(52) U.S. Cl. .............. 530/388.1; 530/387.1; 530/387.7; 530/387.9
(58) Field of Classification Search ........................ None
See application file for complete search history.

(56) References Cited
OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
International Search Report, dated Apr. 24, 2006, corresponding to PCT/KR2005/002493.
Cok, et al., Determination of urinary hippuric acid and o-cresol levels as biological indicators of toluene exposure in shoe-workers and glue sniffers Biomarkers, Mar.-Apr. 2003, vol. 8(2): pp. 119-127.
Inagaki, et al., "An enzyme-linked immunosorbent assay for hippuric acid: its potential application for biological monitoring of toluene exposure" Int Arch Occup Environ Health., 1994, vol. 66(2): pp. 91-95.
Inoue, et al., "Urinary benzylmercapturic acid as a marker of occupational exposure to toluene" Int Arch Occup Environ Health., Jun. 2002, vol. 75(5): pp. 341-347.
Lof, et al., "Toxicokinetics of toluene and urinary excretion of hippuric acid after human exposure to 2H8-toluene" Br J Ind Med., Jan. 1993, vol. 50(1): pp. 55-59.

* cited by examiner

*Primary Examiner*—Sharon Wen
(74) *Attorney, Agent, or Firm*—Christie, Parker & Hale, LLP

(57) ABSTRACT

Provided is a monoclonal antibody specific for hippuric acid. In the present invention, a hippuric acid-carrier protein conjugate is prepared from hippuric acid and BSA or OVA as a carrier protein, using a coupling reagent and a cross-linker. The monoclonal antibody screened according to the present invention has a titer having a standard curve in the concentration range of mg/mL meeting requirements for the permissible exposure limit (PEL) of toluene. The monoclonal antibody exhibits no cross-reactivity with carrier proteins, exhibits higher competitive inhibition in response to an increasing concentration of hippuric acid, and exhibits no cross-reactivity with other proteins contained in the urine. Therefore, the disclosed monoclonal antibody can be usefully employed in a diagnostic kit for detection of hippuric acid which is capable of diagnosing toluene exposure.

3 Claims, 9 Drawing Sheets

SEQ ID NO: 9          FIG.10

```
  1 GCG GCC CAG CCG GCC GAG GTG ATG CTG GTG GAG TCT GGG GCT TCA   45
  1  A   A   Q   P   A   E   V   M   L   V   E   S   G   A   S   15

46 GTG AAG ATA TCC TGC AAG GCT TCT GGT TAC TCA TTC ACT GGC TAC   90
 16  V   K   I   S   C   K   A   S   G   Y   S   F   T   G   Y   30

91 TAC ATG CAC TGG GTG AAA CAA AGC CAT GTA AAG ACC CTT GAG TGG  135
 31  Y   M   H   W   V   K   Q   S   H   V   K   T   L   E   W   45

136 GTT GGA CGT ATT ACT CCT TAT AAT GGT GCT ACT AAC TAC AAC CAG  180
 46  V   G   R   I   T   P   Y   N   G   A   T   N   Y   N   Q   60

181 AAT TTC AAG GAC AAG GCC AGC TTG ACT GTA GAT AAG TCC TCC AGC  225
 61  N   F   K   D   K   A   S   L   T   V   D   K   S   S   S   75

226 ACA GCC TAC ATG GAG TTC CAC AGC CTG ACA TCT GAA GAC TCT GCA  270
 76  T   A   Y   M   E   F   H   S   L   T   S   E   D   S   A   90

271 GTC TAT TAC TGT GTA AGA ATG TAC GCC GAT GTC TGG GGC GCA GGG  315
 91  V   Y   Y   C   V   R   M   Y   A   D   V   W   G   A   G  105

316 ACC TCG GTC ACC GTC TCC TCA GTC AAA ACG ACA CCC CCA TCC GTC  360
106  T   S   V   T   V   S   S   V   K   T   T   P   P   S   V  120

361 TAT CCA CTG GCC CCT GGT GGA GGC GGT TCA GGC GGA GGT GGC TCT  405
121  Y   P   L   A   P   G   G   G   G   S   G   G   G   G   S  135

406 GGC GGT GGC GGA TCG GAA ATT GTT CTC ACC CAG TCT CCA TCC TCC  450
136  G   G   G   G   S   E   I   V   L   T   Q   S   P   S   S  150

451 TTA TCT GCC TCT CTG GGA GAA AGC GTC ACT CTC GCT TGT CGG GCA  495
151  L   S   A   S   L   G   E   S   V   T   L   A   C   R   G  165

496 AGT CAG GAC ATA GGT GGT CGG TTA AAC TGG CTT CAG CAG GAA GCA  540
166  A   S   Q   D   I   G   G   R   L   N   W   L   Q   Q   E  180

541 GAT GGA ACT ATT AAA CGC CTG ATC TAC GCC ACA TCC AGT TTA GAT  585
181  A   D   G   T   I   K   R   L   I   Y   A   T   S   S   L  195

586 TCT GGT GTC CCC AAA AGG TTC AGT GGC AGT AGG TCT GGG TCA GAT  630
196  D   S   G   V   P   K   R   F   S   G   S   R   S   G   S  210

631 TAT TCT CTC ACC ATC AGC AGC CTA GAG TCT GAG GAT TTT GTA GAC  675
211  D   Y   S   L   T   I   S   S   L   E   S   E   D   F   V  225

676 TAT TAT TGT CTA CAA TAT GAT AGA TCT CCG TAC ACA TTC GGA GGG  720
226  D   Y   Y   C   L   Q   Y   D   R   S   P   Y   T   F   G  240

721 GGG ACC AAG CTG GAA ATA AAA CGG GGT GAT GCT GCA CCA ACT GTA  765
241  G   G   T   K   L   E   I   K   R   G   D   A   A   P   T  255

766 GCG GCC GCA
256  V   A   A
```

FIG.11

A. The $V_H$ sequence : SEQ ID NO: 4

```
———————FW1———————        CDR1        ——————FW2——————
EVMLVESGASVKISCKAS      GYSFTGYY     MHWVKQSHVKTLEWVGR
  CDR2        ——————————————FW3——————————————
ITPYNGAT    NYTQNFKDKASLTVDKSSSTAYMEFHSLTSEDSAVYYC
  CDR3    ————FW4————    CH1——————————
VRMYADV    WGAGTSVTVSS    VKTTPPSVYPLAP···
```

B. The $V_K$ sequence : SEQ ID NO: 8

```
——————————FW1——————————        CDR1         ———FW2———
ELVLTQSPSSLSASLGESVTLACR    GASQDIGGRLN    WLQQEADGTIKRLIY
 CDR2    ———————————FW3———————————              CDR3
ATSSLD   SGVPKRFSGRSGDYSSLTISSLESEDFVDDYYC    LQYDRSPYT
——FW4——    CH——————
FGGGTKLEIK  RGDAAPTV···
```

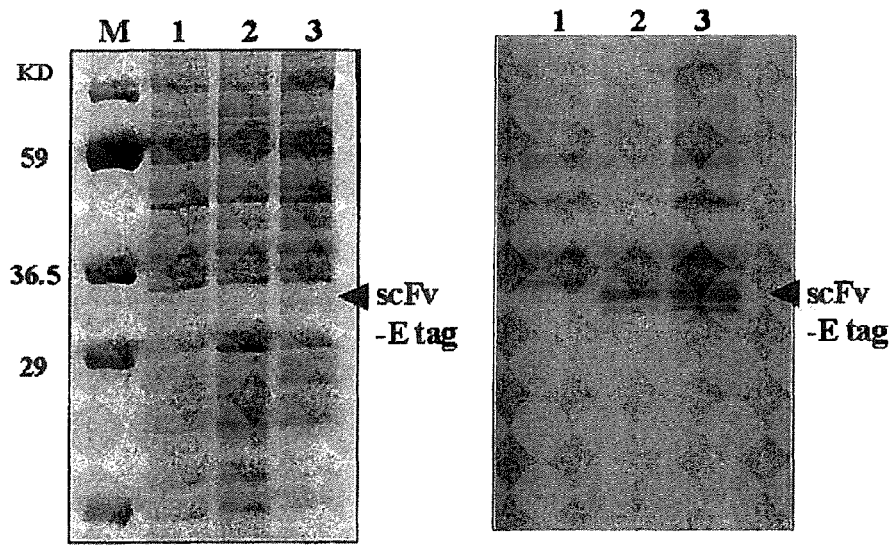

FIG.12

MONOCLONAL ANTIBODY FOR HIPPURIC ACID ANTIGEN

CROSS-REFERENCE TO RELATED APPLICATION

This application is a National Phase Patent Application of International Application Number PCT/KR2005/002493, filed on Jul. 30, 2005, which claims priority of Korean Patent Application Number 10-2005-0067033, filed on Jul. 22, 2005.

TECHNICAL FIELD

The present invention relates to a monoclonal antibody specific for hippuric acid which is one of representative harmful hallucinogenic substances and is the major metabolite of toluene. More specifically, the present invention relates to a monoclonal antibody against hippuric acid, which has a titer in the range of mg/mL meeting requirements for permissible exposure limit (PEL) of toluene, exhibits no cross-reactivity with a carrier protein and exhibits higher competitive inhibition in response to an increasing concentration of hippuric acid, and therefore can be usefully employed to diagnose whether or not humans are exposed to toluene.

BACKGROUND ART

Toluene (methylbenzene, $C_7H_8$) is a colorless aromatic solvent compound having a molecular weight of 92.14 Da, a melting point of −95° C., a boiling point of 110.8° C. and a specific gravity of 0.87 (15° C.), and giving off peculiar smell. Due to the superior solvent power and high evaporation rate, toluene is used in a variety of industrial fields such as formations of paints, printing ink, adhesives, and solvents for agrochemicals, and as a reactant material of various chemical reactions.

Upon exposure to toluene, individuals suffer from adverse effects such as a numbing of the olfactory sense, nausea, the irregular heart beat and the feeling of alcoholic intoxication. In severe cases, toluene exposure may cause hepatic and renal damage, neuropathy and cerebral injury. In recent years, the incidences of a rare occupational disease with symptoms of stiffening and sclerosing of all extremities and shoulders as well as the lungs were reported in workers who had been engaged in the adhesion work of tennis balls for about 10 years in a domestic tennis ball factory. It was found that the pathogenic cause of this disease was toluene intoxication due to the presence of toluene contained in adhesives.

At present, according to relevant provisions of the Industrial Safety and Health Act (ISH Act), the permissible exposure limit (PEL) of toluene is prescribed as TWA (Time-Weighted Average): 100 ppm. According to the Enforcement Decree of the Korea Foul Odor Prevention Act (effective from Feb. 20, 2005), the toluene emission limit will be restricted to within 30 ppm for industrial areas and within 10 ppm for other areas, from Feb. 20, 2008. Therefore, in order to comply with such environmental legislations for permissible discharge standards of toluene, factories and plants using toluene are forced to install local exhaust or process enclosure ventilation systems and to provide the respiratory protective devices in workplaces.

Meanwhile, in addition to such industrial problems associated with emission of toluene, inhalation of glue containing large amounts of toluene is a pathosociological phenomenon which is peculiarly observed in developing countries including Korea. Misuse of glue, which is committed particularly by young people, in order to experience phantasmagoria and hallucination similar to those appearing upon administration of narcotic drugs such as marijuana smoking and cocaine inhalation, is a serious social ill. The harmful evil influence of glue-sniffing on society and individuals may be more serious than that of the above-mentioned narcotic drug abuse, because glue-sniffing may cause incurable sequelae due to schizophrenia or brain atrophy caused by cerebral damage.

As discussed hereinabove, strictly strengthened regulations and practices in terms of industrial safety have led to an increasing demand for the development of a method which is capable of confirming exposure of workers to hazardous environmental factors under working conditions, such as toluene, and on the other hand, which is capable of determining whether young people and the like have inhaled toluene, in order to prevent and inhibit drug misuse and abuse.

Conventional methods currently used are based on determination of an amount of toluene per se or hippuric acid as a metabolite of toluene, which is present in the blood or urine, using analytical chemical methods. However, the performance of such determination methods have suffered from a need of expensive equipment such as the gas chromatography/mass spectroscopy (GC/MS) or the high performance liquid chromatography (HPLC) as well as highly skilled experts who can skillfully handle such equipments and can analyze the results thus obtained. Further, since application of such methods should involve long time-consuming processes such as preparation and concentration of samples through solvent extraction, it was hardly possible to apply such methods to large-sample groups such as worker groups, student groups or soldier groups.

In order to overcome the above-mentioned disadvantages and obtain objective examination results within a short period of time and with a simple method, use of immunoassays using antigen-antibody reactions is widely recommended. For detection of hippuric acid via the immunoassays, a specific antibody is necessary which is specifically reactive with hippuric acid present in the body fluid, particularly urine, but is not reactive with other components. However, when a molecular weight of an antigen is less than 3,000 Da, the activation of an immune system is not sufficiently achieved and therefore it is difficult to elicit the production of a specific antibody directed against the target antigen (Harlow and Land, 1988). In this respect, since hippuric acid has a low molecular weight of 179 Da and low immunogenicity, it is difficult to obtain the desired antibody with conventional immunization methods widely used in the art.

As already mentioned hereinbefore, the permissible exposure limit (PEL) of toluene in Korea is prescribed as 100 ppm (TWA) which corresponds to about 2.5 g/g of creatinine, as the content of hippuric acid in the urine is expressed in terms of creatinine in the urine. Meanwhile, according to clinical data from The Kyung-Hee University Medical Center (Seoul, Korea), the ordinary people excrete 1.6 L/day of urine in normal state. When it was calculated by taking into consideration 25% deviation between individuals, and by taking the above base value, i.e., 2.5 g/g of creatinine, as an average value, the urination amount is in the range of 1.2 to 2.0 L and therefore the amount of hippuric acid in the urine is about 1.25 to 2.08 mg/mL. As such, the hippuric acid-specific antibody intended for determination of this base value should not have a standard curve dynamic range in a low concentration (level of ng/mL or μg/mL) as typically shown in conventional antibodies, and therefore it is necessary to adjust the level of the antibody against hippuric acid to have the standard curve dynamic range (level of mg/mL) at which the presence/absence of toluene inhalation can be determined within the above ranges.

Upon absorption of toluene into the body, 20% of absorbed toluene is naturally eliminated via the respiratory system, whereas the remaining 80% of toluene is converted, via the microsomal mixed function oxidase system, into benzoyl alcohol which is, in turn, oxidized into benzoic acid via oxidative metabolism by alcohol dehydrogenase and aldehyde dehydrogenase. Finally, the resulting benzoic acid conjugates with glycine to form hippuric acid which is then excreted into the urine. In this connection, since the presence of benzoic acid in the body may also be due to food intake, a diagnostic strip according to the present invention should not exhibit detection sensitivity for trace amounts of hippuric acid which is excreted into the urine by means of benzoic acid absorbed into the body via daily dietary intake. Therefore, the hippuric acid-directed antibody is not simply intended to determine the presence of hippuric acid, and is thus preferably designed to be capable of determining whether or not hippuric acid is present over a predetermined level, depending upon various diagnostic purposes. That is, the antibody is preferable which can readily determine a sample having a diagnostic cut-off concentration (sensitivity level) of hippuric acid of more than about 1.25 mg/mL. Below 1.25 mg/mL of hippuric acid, there may be a problem of detecting excretion of hippuric acid due to other factors including dietary intake.

Until now, a great deal of attention has been focused only on the development of monoclonal antibodies (MAbs) which are capable of detecting a level of from ng/mL to μg/ml by a competitive assay. This is because insensitive antibodies having a low detection sensitivity of mg/mL level are highly cross-reactive with other antigens (proteins and the like) due to low specificity, and therefore are difficult to be used in diagnostic strips. As such, there is an urgent need for the development of an antibody having a low cross-reactivity, a specific reactivity only with hippuric acid and a titer capable of detecting hippuric acid at the level of mg/mL falling within the permissible exposure limit of toluene, with discrimination from hippuric acid remaining in the body via daily dietary intake.

Further, the existing methods for production of monoclonal antibodies are confined to animal experiments involving the use of experimental animals such as mice and the like, take a long period of time for the production of antibodies and require labor-intensive work for the selection and screening of large numbers of cells, as well as sufferings from difficulties in the control of specificity and affinity of the produced antibodies. To this end, there is a need for the development of a technique which is capable of securing genes for an antibody of interest using DNA recombinant techniques without animal experiments involving the use of experimental animals such as mice and the like, producing the desired monoclonal antibody in E. coli within a short period of time and engineering the specificity and affinity of the thus-produced antibody.

DISCLOSURE

Technical Problem

Therefore, the present invention has been made in view of the above problems, and it is an object of the present invention to provide an antibody having a specific reactivity only with hippuric acid due to a low cross-reactivity, and a titer capable of detecting hippuric acid at the mg/mL level falling within the permissible exposure limit of toluene, with discrimination from hippuric acid remaining in the body via daily dietary intake.

It is another object of the present invention to develop a technique which is capable of securing genes for an antibody of interest using DNA recombinant techniques without animal experiments such as the use of experimental animals including mice, producing the desired monoclonal antibody in E. coli within a short period of time and engineering the specificity and affinity of the thus-produced antibody.

Technical Solution

In accordance with an aspect of the present invention, the above and other objects can be accomplished by the provision of a heavy chain variable region of a monoclonal antibody against a hippuric acid antigen, comprising a CDR1 region having an amino acid sequence set forth in SEQ. ID. NO: 1, a CDR2 region having an amino acid sequence set forth in SEQ. ID. NO: 2 and a CDR3 region having an amino acid sequence set forth in SEQ. ID. NO: 3.

As used herein, CDRs (complementarity determining regions), which structurally constitute antigen-binding sites within variable regions of the monoclonal antibody, are important parts for determining the specific complementarity with an antigen of interest. If the antibody retains sequences of these CDRs intact, it is possible to produce various antibody libraries via the replacement of sequences in other regions without affecting the antigen-binding affinity (Biochemistry, 2003 Feb. 18; 42(6):1517-28). In Examples of the present invention, amino acid sequencing of the heavy chain variable regions of the monoclonal antibody was carried out, and the regions assigned to CDRs and FRs were then analyzed using on-line tools (IMGT/V-QUEST database) which are accessible via the Internet (see FIG. 11A). Throughout the present specification, amino acid sequences of CDR1, 2 and 3 of the heavy chain variable region are represented by SEQ. ID. NO: 1, SEQ. ID. NO: 2 and SEQ. ID. NO: 3, respectively. Preferably, the heavy chain variable region of the monoclonal antibody according to the present invention is comprised of an amino acid sequence set forth in SEQ. ID. NO:4

In accordance with another aspect of the present invention, there is provided a light chain variable region of a monoclonal antibody against a hippuric acid antigen, comprising a CDR1 region having an amino acid sequence set forth in SEQ. ID. NO: 5, a CDR2 region having an amino acid sequence set forth in SEQ. ID. NO: 6 and a CDR3 region having an amino acid sequence set forth in SEQ. ID. NO: 7.

In Examples of the present invention, amino acid sequencing of the light chain variable regions of the monoclonal antibody was carried out, and the regions assigned to CDRs and FRs were then analyzed using on-line tools (IMGT/V-QUEST database) which are accessible via the Internet (see FIG. 11B). Throughout the present specification, amino acid sequences of CDR1, 2 and 3 of the light chain variable region are represented by SEQ. ID. NO: 5, SEQ. ID. NO: 6 and SEQ. ID. NO: 7, respectively. Preferably, the light chain variable region of the monoclonal antibody according to the present invention is comprised of an amino acid sequence set forth in SEQ. ID. NO: 8.

In accordance with yet another aspect of the present invention, there is provided a monoclonal antibody against a hippuric acid antigen, comprising the heavy chain variable region according to the present invention and the light chain variable region according to the present invention, as described above.

As will be illustrated in Examples of the present invention hereinafter, it is demonstrated that the monoclonal antibody having the above-mentioned variable regions has a titer having the standard curve dynamic range at the concentration level of mg/mL meeting requirements for the permissible exposure limit (PEL) of toluene, exhibits no cross-reactivity with a carrier protein and exhibits higher competitive inhibition in response to an increasing concentration of hippuric acid, and therefore can be usefully employed in a diagnostic kit for detection of hippuric acid which is capable of diagnosing the toluene exposure.

Preferably, the monoclonal antibody of the present invention is a single-chain antibody fragment, i.e., scFv (single chain variable fragment) wherein the heavy chain variable region and the light chain variable region are linked by a peptide linker having a predetermined length. In this case, it is possible to produce a desired monoclonal antibody in E. coli within a short period of time, using DNA recombinant techniques without animal experiments such as the use of mice, to secure genes for the thus-produced antibody and to engineer the specificity and affinity of the antibody.

More preferably, in the monoclonal antibody of the present invention, the single chain variable fragment (scFv) is comprised of an amino acid sequence set forth in SEQ. ID. NO: 9. The amino acid sequence of SEQ. ID. NO: 9 is deduced from the sequence of the scFv gene cloned in Examples of the present invention which will be illustrated hereinafter (see FIG. 10).

Advantageous Effects

The monoclonal antibody screened according to the present invention has a titer having a standard curve in the concentration range of mg/mL meeting requirements for the permissible exposure limit (PEL) of toluene, exhibits no cross-reactivity with a carrier protein, exhibits higher competitive inhibition in response to an increasing concentration of hippuric acid and also exhibits no cross-reactivity with other proteins contained in the urine, and therefore can be usefully employed in a diagnostic kit for detection of hippuric acid which is capable of diagnosing the toluene exposure. Further, in terms of providing a technical basis, the present invention is of great significance in the paint that it is possible to produce the desired monoclonal antibody in E. coli within a short period of time, using DNA recombinant techniques without animal experiments involving the use of experimental animals such as mice and the like, through the cloning of a gene coding for a single chain variable fragment (scFv) retaining the variable regions of the monoclonal antibody to thereby secure the gene for the antibody, and it is also possible to engineer the specificity and affinity of the thus-produced antibody.

DESCRIPTION OF DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which:

FIG. 10 shows a base sequence and a deduced amino acid sequence (SEQ ID NO: 9) of scFv gene;

FIGS. 11A-11B show amino acid sequences of variable regions ($V_H$ and $V_K$FIGS. 11A, 11B, respectively) of the heavy chain (kappa chain) deduced from scFv; and FIG. 12 is a photograph showing the results of SDS-PAGE and Western blot analysis of the scFv expression.

BEST MODE

Figure 1:
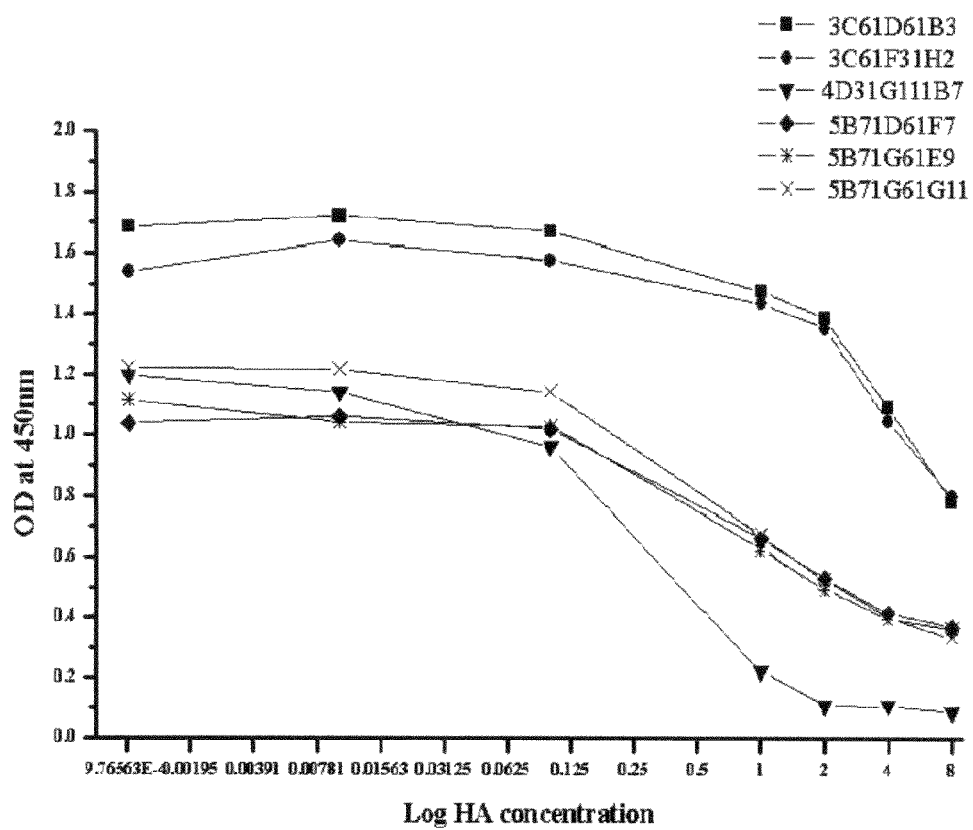
FIG. 1 is a graph showing the results of the competitive ELISA for monoclonal antibodies directed against hippuric acid (HA)

Hereinafter, the present invention will be described in more detail.

The object of the present invention resides in construction and characterization of a monoclonal antibody against hippuric acid (HA), and thereby preparation of a raw material for a diagnostic kit which is capable of detecting urinary hippuric acid by a simple and easy method with safety and high-sensitivity.

In order to use hippuric acid having a low molecular weight as a target immunogen, among a variety of immunogens for antibody production, hippuric acid should be linked directly or linked via a cross-linker to a carrier protein having a high molecular weight (Harlow and Lane, 1988). Typically, keyhole limpet hemocyanin (KLH), bovine serum albumin (BSA) or ovalbumin (OVA) is employed as the carrier protein. The present invention has employed hippuric acid, and BSA and OVA as carrier proteins. In order to elicit immune reactions, HA was conjugated with bovine serum albumin (BSA) or ovalbumin (OVA) as the carrier protein, and the resulting products were confirmed by 10% non-denatured PAGE. After BALB/c mice were immunized with the BSA-HA conjugate as an immunogen, splenocytes were collected and fused with the mouse myeloma cells (SP2/0). The thus-fused cells were cultured in a selection medium (HAT medium) for the primary selection, and then the cell lines producing antibodies directed against HA were selected from cultured cells, using a limiting dilution method. Herein, the selection of the desired cell lines was carried out using an enzyme linked immunosorbent assay (ELISA).

Finally, 19 monoclonal antibody-producing cell lines were obtained, and out of monoclonal antibodies produced from these cell lines, 6 species having a high titer were selected and subclass isotyping of the antibodies thus screened were determined. From the analysis results, it was confirmed that 6 species of antibodies all produce $IgG_1$ subclass antibodies having a kappa (κ) light chain. Upon confirming the crossreactivities of individual monoclonal antibodies with carrier proteins using the ELISA method, it was revealed that individual monoclonal antibodies exhibit no cross-reactivity with both carrier proteins (BSA and OVA). In particular, it was confirmed that the cell line 4D31G111B7-produced monoclonal antibody exhibit no cross-reactivity with carrier proteins (BSA and OVA) even by Western blot analysis and are specifically reactive only with HA having a molecular weight of 179 Da. Consequently, it is believed that the cell line 4D31G111B7-produced monoclonal antibody can be used to detect HA present in the urine.

Ascites was produced from the cell line 4D31G111B7, and antibody was purified by the protein G affinity column chromatography technique. It was observed that the cell line 4D31G111B7-produced monoclonal antibody exhibits an about 10-fold decrease in % binding capacity to an antigenic conjugate, i.e., from 79.3% to 7.9%, in the HA concentration range of 0.5 to 0.0078 mg/mL, when the concentration of the antigenic conjugate for an assay is 2 µg/mL. That is, it was confirmed that present antibody have a sufficient binding capacity to HA itself. Upon performing a competitive ELISA between the antigenic conjugate and HA using the purified antibody, it was confirmed that the antibody is readily reactive with HA.

Based on these experimental results, it is expected that the monoclonal antibodies established according to the present invention can be used as a raw material for preparation of a diagnostic kit which detects HA in the urine. The antibody used in the diagnostic kit is in the form of an antibody-colloidal gold conjugate, and undergoes antigen-antibody reaction with HA which is a metabolite of toluene and about more than 80% of which is present in the sample (urine), thereby resulting in binding of the antibody to HA. When large amounts of HA are present in the urine, HA interacts with the antibody with colloidal gold strongly and the HA-antibody-colloidal gold complex migrates upward on the membrane of the diagnostic kit by the capillary action. HA-antibody-colloidal gold complex continuously migrates without any reaction even though it encounters the antigens immobilized on the membrane. If there is no HA in the sample, antibody encounters the membrane-immobilized antigens and therefore the antibody-colloidal gold conjugate will be visible.

As already discussed hereinbefore, application of the conventional methods for production of monoclonal antibodies is restricted to animal experiments such as the use of mice or the like, takes a long period of time for production of antibodies and requires labor-intensive processes for the selection of large numbers of cells, as well as suffering from many difficulties in the control of specificity and affinity of the thus-produced antibodies. In order to solve such problems suffered by conventional methods, the present invention establishes a basic technology which is capable of obtaining genes for an antibody of interest using DNA recombinant techniques, producing the desired monoclonal antibody in *E. coli* within a short period of time and engineering the specificity and affinity of the thus-produced antibody.

At the present time, the majority of currently available immunoassays usually use antibodies as detection means of the target material. The variable region of the antibody, called an antibody arm, has a detection function. Genes coding for the variable regions of the functional heavy and light chains were amplified by an RT-PCR (Reverse Transcriptase-Polymerase Chain Reaction) technique, using the already-established cell lines producing the hippuric acid-directed monoclonal antibody. The primer used herein was a degenerated primer made up of any combinations which is capable of meeting almost the total number of cases for antibodies that can be produced in mice. Then, the thus-amplified genes for the variable regions of the heavy and light chains were amplified by Splicing by Overlap Extension-PCR(SOE-PCR) technique using a linker DNA, thereby completing a single chain variable fragment (scFv). The resulting gene amplification product was cloned into the vector pCANTAB5E, thereby confirming a base sequence thereof.

After inducing the expression of the single chain variable fragment (scFv) for 9 hours, the expression of scFv was confirmed by SDS-PAGE and Western blot analysis. After the large-scale expression of the soluble scFv which was found to have a size of about 32 kDa, the-thus expressed antibodies were purified using HiTrap anti-E tag affinity column chromatography technique. When the affinity of the purified soluble scFv for the hippuric acid antigen was measured by ELISA (Enzyme Linked Immunosorbent Assay), the antibody titer was detectable until about 10-fold dilution. Therefore, the present invention will have a profound significance in the point that a technical basis is provided which is capable of overcoming various problems suffered by the conventional prior art methods for the production of monoclonal antibodies, via construction of the recombinant scFv utilizing only the variable regions of the antibody through the use of mRNA isolated from the cell line producing hippuric acid-directed antibodies and the mass expression of the thus-constructed recombinant scFv, and is capable of controlling the specificity and affinity of the antibody via acquisition of genes for the antibody of interest.

The thus-produced scFv is a small antibody having a size of about 30 kDa and has a structure similar to that of the antigen-binding site of the parent monoclonal antibody from which the scFv antibody was derived (Thirion et al., 1996), and heavy and light chain variable regions of the antibody are linked via a short and flexible polypeptide linker. The linker is composed of a $(Gly_4Ser)_3$ sequence wherein a Gly residue confers flexibility and a Ser residue confers slight solubility (Huston et al., 1988). In addition, it was also found through the NMR analysis that this sequence exhibits high fluidity and flexibility (Kortt et al., 1994). Further, the linker has a length enough to connect a distance ranging from a C-terminus of one domain to an N-terminus of another domain, and may interact with an antibody Fv fragment via formation of a loop which will be fitted precisely into the gap between two domains (Stemmer et al., 1993). The antibody Fv fragment retains a functional antigen-binding site intrinsic to the parent monoclonal antibody, and can maintain specific affinity for the antigen (Hudson, 1998). The single chain variable fragment has advantages such as stability similar or comparable to that of proteins, capability to improve specific affinity by modification of an amino acid sequence and feasibility of large-scale production in *E. coli* expression systems.

MODE FOR INVENTION

EXAMPLES

Now, the present invention will be described in more detail with reference to the following examples. These examples are provided only for illustrating the present invention and should not be construed as limiting the scope and spirit of the present invention.

Example 1

Synthesis of Immunogen and Assay Antigen

Hippuric acid (HA) (Sigma, USA) was conjugated with bovine serum albumin (BSA) (Product No. 21555, Sigma, USA) or ovalbumin (OVA) (Product No. A-5378, Sigma, USA) as a carrier protein. The resulting BSA-HA conjugate was used as an immunogen, and the resulting OVA-HA conjugate was used as an assay antigen. Attachment of hippuric acid to the carrier protein was carried out by a direct binding method and a method of forming a conjugate using the cross-linkers ACA and SA (Pilch and Czech, 1979). First, hippuric acid, DCC and NHS were dissolved in DMF, were reacted with gentle stirring at room temperature for 2 hours, and centrifuged. The resulting supernatant was added to a solution in which carrier proteins were dissolved, and the reaction materials were reacted with gentle stirring at room temperature for 4 hours. After centrifugation and removal of precipitates thus formed, the supernatant was dialyzed two times to remove the remaining DMF, thereby preparing polymer products (BSA-HA and OVA-HA) in which hippuric acid was attached directly to proteins. For preparation of HA-carrier protein conjugates using the cross-linkers, hippuric acid, DCC and NHS were dissolved in DMF, were reacted with gentle stirring at room temperature for 2 hours and centrifuged. The resulting supernatant was mixed with a solution in which ACA or SA was dissolved, and the mixtures were reacted with gentle stirring at room temperature for another 2 hours. After centrifugation and removal of precipitates thus formed, the supernatant was dialyzed two times to remove the remaining DMF and ACA or SA. Formation of the carrier protein-HA conjugates was confirmed by electrophoresis using 10% Native gel, and the conjugation yield was determined by Bicinchoninic Acid (BCA) Protein Assay.

Example 2

Immunization of Mice

With modification of methods described by Kohler and Milstein (1975), and Doyen et al (1985), mice were immunized by combination of intraperitoneal injection and subcutaneous injection. For this purpose, 109 µl of a BSA-HA conjugate (based on BSA concentration) and 46 µl of a BSA-ACA-HA conjugate (based on BSA concentration) were respectively mixed with complete Freund's adjuvants in a mixing ratio of 1:1. BALB/c male mice (Samtaco, Osan, Korea) (n=6, 5-week old, and acclimated for 1 week) were divided into 3 groups, each consisting of 2 animals. Mice of each group were immunized by intraperitoneal injection of each mixture. Here, an immunizing amount of the mixtures did not exceed a dose of 300 µl/animal. Then, animals were immunized three times with equal amounts of immunogens in admixture with incomplete Freund's adjuvants, at an interval of 2 weeks after initial immunization, In order to confirm whether immunization of animals was successfully achieved, an antibody titer was determined by an indirect ELISA method using the OVA-HA conjugate. The antibody titer determined in anti-sera of immunized BALB/c mice was calculated by determining each titer of 2 mice immunized with the BSA-HA conjugate and 2 mice immunized with the BSA-ACA-HA conjugate, and dividing the sum of titer by the number of animals. When the antibodies were 1000-fold diluted, an average antibody titer of 4 animals was 2.413. Whereas, the non-immunized BALB/c mouse group exhibited the antibody titer of 0.102, as determined under the same conditions. Upon using each conjugate as the immunogen, it was observed that the BSA-HA conjugate exhibits the highest antigenicity. When animals were immunized up to three times with the BSA-HA conjugate, sequential increases were observed in production of antibodies.

Example 3

Cell Fusion (1) Preparation of Immunized Lymphocytes

Antibody titer of anti-sera of immunized mice was determined by an indirect ELISA method, and mice showing the highest antibody titer were selected. The selected mice were treated by intravenous injection of 100 µg of an HA-BSA conjugate, dissolved in PBS 3 days prior to cell fusion, into tail veins of animals. The thus-treated animals were sacrificed by cervical dislocation and disinfected with 70% ethanol. An abdominal incision was made and spleens were removed from the animals. The spleens were gently washed with 10 mL of RPMI 1640 medium (Product No. 31800-022, Gibco BRL, USA), and spleen lymphocytes were collected in 30 mL of RPMI 1640 medium, using a cell dissociation sieve-tissue grinder kit. The cells were sedimented by centrifugation at 400×g, and leucocyte components were hemolyzed and separated using a red blood cell lysis buffer in which 8.3 g/L of ammonium chloride was contained in a 0.01M Tris-HCl buffer, pH 7.5 (Product No. R-7757, Sigma, St. Louis, USA). Cellular components thus separated were washed three times with 30 mL of RPMI 1640 medium. The thus-precipitated cells were homogeneously distributed in 10 mL of fresh RPMI 1640 medium, and stored in an incubator at 37° C. during preparation of plasmacytoma cells.

(2) Culture of SP2/0 Plasmacytoma Cells

SP2/0 plasmacytoma cell line (ATCC No. CRL-1646), which is commonly used in expression of monoclonal antibodies, was cultured for use in cell fusion. This cell line is a mutant cell line, which is incapable of producing immunoglobulins and is deficient in hypoxanthine guanine phosphoribosyl transferase (HGPRT). This cell line was sub-cultured in RPMI 1640 medium (Product No. R6504, Sigma, St. Louis, USA) containing 10% fetal bovine serum (Product No. 15-010-0500V, Trace, A.C.N., Australia), sodium bicarbonate, 100 µg/mL of penicillin streptomycin (Product No. 15140-122, Gibco BRL, New York, USA) and Fungi-zone (Product No. 15295-017, Gibco BRL, New York, USA), and was aliquoted to a fresh medium in a 1:1 ratio one day prior to cell fusion, such that cells can be maintained in healthy conditions.

(3) Cell Fusion

Cell fusion was carried out by Milstein et al. method (1979) which is a modified version of Kohler and Milstein method (1975). Pre-cultured plasmacytoma cells were harvested, sedimented by centrifugation at 400×g, and washed three times with 30 mL of RPMI 1640 medium. Then, the sedimented cells were homogeneously distributed in 10 mL of fresh RPMI 1640 medium. The prepared spleen lymphocytes and plasmacytoma cells were stained with a 0.04% trypan-blue solution (Product No. T-8154, Sigma, St. Louis, USA) and the viable cell count was performed using a hemocytometer. Plasmacytoma cells and spleen lymphocytes were mixed in a number ratio of 10⁷:10⁸, and the mixed cells were washed with RPMI 1640 medium. After final washing was complete, the supernatant was completely removed and the tube containing the precipitated cells thus obtained was gently tapped with fingers, such that cells can be intimately mixed. Then, 1 mL of a 50% (w/v) PEG/DMSO (Product No.

P-7306, Sigma, St. Louis, USA) solution was added dropwise to the cell mixture at a flow rate of 1 mL/min, while maintaining the temperature of the tube at 37° C., followed by addition of 30 mL of RPMI 1640 medium at a flow rate of 3 mL/min. Cells, which have completed cell fusion, were sedimented and pooled by centrifugation at 400×g for 10 min. In order to pick out fused cells only, the cells were suspended in HAT (Product No. 31062-011, Gibco BRL, USA) RPMI medium (containing 20% FBS added) designed by Littlefield (1964), and 50 µl/well of cells was aliquoted into 96-well plates (n=5) containing feeder cells. 50 µl/well of HAT RPMI medium supplemented with 20% FBS was aliquoted thereto, followed by incubation at 37° C. for 24 hours in the presence of 5% $CO_2$ and addition of 50 µl/well of HAT medium. Thereafter, the culture medium was replaced every 3-4 days with 100 µl/well of HAT RPMI medium supplemented with 20% FBS, while observing proliferation of fused cells under the inverted microscope (IMT2-21-W-PM20-35DX2, Olympus, Japan).

Example 4

Selection of Monoclonal Antibody-Secreting Cell Lines

When cells have grown enough to occupy 10 to 20% of the well bottom area via continuous observation of cell growth under the inverted microscope after cell fusion, the medium stock was taken from the top layer of the well and the antibody titer was determined using an indirect ELISA method with modification of Engvall and Pelmann method (1972) and an OVA-HA conjugate. Wells showing a difference of an OD value of more than 0.5 in the antibody titer, as compared to a negative control, were selected. When cells grown to an about 50% area of the well, they were transferred to and cultured in 24-well plates. Cells, grown to 10 to 20% in the 24-well plates, were subjected again to the determination of the antibody titer by the indirect ELISA method, and wells exhibiting a high antibody titer and continued good state of cells were selected. Cells were aliquoted at a cell density of 5 cells/well to 96-well plates by a limiting dilution method and cultured. Thereafter, cells were aliquoted again to a cell density of 0.5 cell/well by the limiting dilution method, thereby establishing monoclonal antibody-secreting cell lines.

The antibody-secreting cells thus obtained were cultured in 96-well plates and the antibody titer was determined by ELISA. From Plates 2, 3, 4 and 5 among 5 plates, it was confirmed that a total of 6 species of fused cells having a high value of 1.857, 0.932, 0.829, 1.867, 0.745, 1.477 and 1.695 were cultured. Thereafter, 6 species of fused cells were diluted to a cell density of 5 cells/well in a primary limiting dilution, and diluted to a cell density of 0.5 cells/well in a second limiting dilution, respectively. After the cells thus diluted were cultured, 19 species of monoclonal antibody-secreting cell lines were finally obtained (see Table 1). Table 1 shows the titer and saturation titer of fused cells after second limiting dilution. Titers for OVA-HA conjugates of the supernatants of individual wells were determined by an indirect ELISA. Anti-HA serum and PBS or normal medium were used as a positive and negative controls, respectively. Upon performing the indirect ELISA, it was confirmed that 19 species of the established monoclonal antibodies exhibit the titer of maximum 1.427 (3C61D61B3), and the established monoclonal antibodies all exhibit the titer higher than the negative control, and equal to or higher than the positive control. However, if the titer is excessively high, it is difficult to selectively detect hippuric acid in the range of mg/mL meeting requirements for permissible exposure limit thereof, with discrimination from hippuric acid remaining in the body due to daily food intake. Therefore, the cell line 4D31G111B7 exhibiting a moderate titer was selected as the monoclonal antibody-secreting cell line.

TABLE 1

| Cell Line | Titer | Saturation |
|---|---|---|
| 3C61D61B3 | 1.427 | 0.279 |
| 3C61G111E11 | 1.431 | 0.339 |
| 3C61G111G3 | 1.498 | 0.315 |
| 3C61F31H2 | 1.327 | 0.293 |
| 4D31G111B7 | 1.283 | 0.107 |
| 4D31G111B2 | 1.232 | 0.126 |
| 4D31G111E9 | 1.267 | 0.133 |
| 4D31G111A12 | 1.283 | 0.146 |
| 5B71G61C10 | 0.481 | 0.083 |
| 5B71G61G11 | 0.483 | 0.074 |
| 5B71G61D5 | 0.524 | 0.080 |
| 5B71G61E9 | 0.549 | 0.073 |
| 5B71G61F8 | 0.588 | 0.081 |
| 5B71G91F7 | 0.437 | 0.075 |
| 5B71D61F7 | 0.629 | 0.147 |
| 5B71D61B8 | 0.659 | 0.130 |
| 5B71D71B1 | 0.457 | 0.077 |
| 5B71D111F9 | 0.506 | 0.112 |
| 5B71D111F5 | 0.442 | 0.066 |

When competitive ELISA was performed to examine whether 19 species of monoclonal antibodies, simultaneously established by the above-performed indirect ELISA, also effectively function against the hippuric acid antigen, it was shown that the cell line 3C61G111E11 having the highest titer exhibits the antigen-antibody reactivity (degree of saturation) of 0.339 for the hippuric acid antigen. Out of 19 species of cell lines, the cell line 4D31G111B7, the replication origin of which was derived from the cell line 4D31G11, exhibited a high titer of 1.283 as determined by indirect ELISA, and also exhibited a high degree of saturation of 0.107 in the competitive ELISA test (due to direct reaction of hippuric acid with the monoclonal antibody, there was no encounter with antibodies coated on the wells) (see Table 1).

Example 5

Titer Determination of 6 Cell Lines via Competitive ELISA

The object of the present invention is to find a cell line producing the highest competition among multi-species of the established monoclonal antibodies, and thereby plot a standard curve. Utilizing culture media containing IgG secreted by cell lines, a concentration of hippuric acid was determined from 8 mg/mL to 0.001 mg/mL. It was determined that the monoclonal antibody-producing cell line 4D31G111B7 has the lowest value of 0.090 for high concentrations of hippuric acid, and has a high value of 1.291 in the absence of hippuric acid, thus representing that the monoclonal antibody produced from this cell line is most competitive with an antibody directed against hippuric acid. These results mean that the antibody secreted by the cell line 4D31G111B7 is an antibody directed against hippuric acid. Therefore, the present inventors have decided to use the cell line 4D31 G111B7 in preparation of ascitic fluid for mass production of antibodies (FIG. 1). FIG. 1 is a graph showing the results of competitive ELISA for monoclonal antibodies directed against hippuric acid (HA). Each monoclonal antibody supernatant was used as a primary antibody and was pre-incubated with HA at 37° C. for 30 min. The pre-incubation mixture was transferred to a well, pre-coated with an OVA-HA conjugate, and incubated at 37° C. for 30 min. Color development with TMB substrate was carried out at room temperature for 5 min.

Example 6

Purification of Monoclonal Antibodies (MAbs)

In order to obtain large quantities of monoclonal antibodies, MAb-secreting cells were inoculated into the abdomen of BALB/c mice from which ascites was then collected, and 4D31G111B7 antibodies were purified by affinity column chromatography using a protein G column. A 1 mL protein G column (Product No. 54840-U, Supelco, Bellefonte, USA) was equilibrated by washing with a 20 mM sodium phosphate buffer (pH 7.0), and 1 mL of an ascites sample, fractionally precipitated with ammonium sulfate, was added to the column. Thereafter, the column was washed with the same buffer to remove proteins not bound to protein G, and the bound IgG was eluted with a 0.1M Glycine-HCl buffer (pH 2.7). A 1M Tris-HCl buffer (pH 8.0) was added to the thus-eluted sample in an amount corresponding to 1/10 volume of the eluate, thereby returning the pH value of the sample to an initial value (Kerr et al., 1994). The eluted sample was concentrated to a volume of 200 to 500 µl, using a 2 mL concentrator (Product No. 99VS0248, Vivascience, USA).

Example 7

Specificity of Monoclonal Antibodies (1) Determination of Cross-Reactivity of Monoclonal Antibodies with Carrier Proteins via Indirect ELISA BSA and OVA, which are carrier proteins used in conjugate synthesis, were respectively diluted to a concentration of 1 µl/mL in a 0.01M carbonate buffer (pH 9.6) and 200 µl/well of the thus-diluted carrier proteins were aliquoted into a 96-well microtiter plate (Product No. 2580, Costar, Corning, USA), followed by reaction at 4° C. overnight. Subsequent procedures were the same as previously described in indirect ELISA, and a monoclonal antibody (4D31G111B7) culture was treated instead of sera. In order to determine cross-reactivity with the carrier proteins, wells were coated with BSA, OVA, casein and OVA-HA, respectively. Indirect ELISA has confirmed that the monoclonal antibody-secreting cell line 4D31G111B7 used in the preparation of ascitic fluid exhibits no cross-reactivity with the carrier proteins BSA and OVA, and a blocking protein, casein used in indirect ELISA (see Table 2). Table 2 shows the determination results for cross-reactivity of anti-HA monoclonal antibody with the carrier proteins.

TABLE 2

| Cell Line | Dilution | BSA* | OVA** | CASEIN | NON | OVA-HA |
|---|---|---|---|---|---|---|
| Antibody 4D31G111B7 | 1/10² | 0.154 | 0.057 | 0.078 | 0.159 | 1.307 |
|  |  | 0.151 | 0.071 | 0.052 | 0.192 | 1.200 |
|  | 1/10³ | 0.050 | 0.056 | 0.042 | 0.131 | 1.089 |
|  |  | 0.048 | 0.045 | 0.040 | 0.063 | 1.103 |
|  | 1/10⁴ | 0.042 | 0.043 | 0.044 | 0.120 | 0.496 |
|  |  | 0.042 | 0.047 | 0.430 | 0.110 | 0.573 |
|  | 1/10⁵ | 0.041 | 0.055 | 0.041 | 0.115 | 0.163 |
|  |  | 0.042 | 0.070 | 0.042 | 0.111 | 0.217 |
|  | 1/10⁶ | 0.040 | 0.066 | 0.041 | 0.101 | 0.175 |
|  |  | 0.040 | 0.079 | 0.042 | 0.096 | 0.107 |
|  | PBS | 0.040 | 0.043 | 0.042 | 0.091 | 0.103 |
|  |  | 0.042 | 0.047 | 0.042 | 0.090 | 0.060 |

TABLE 2-continued

| Cell Line | Dilution | BSA* | OVA** | CASEIN | NON | OVA-HA |
|---|---|---|---|---|---|---|
| Normal | 1/10² | 0.068 | 0.071 | 0.066 | 0.090 | 0.182 |
|  |  | 0.059 | 0.070 | 0.062 | 0.075 | 0.146 |
|  | 1/10³ | 0.052 | 0.060 | 0.051 | 0.074 | 0.065 |
|  |  | 0.048 | 0.046 | 0.047 | 0.060 | 0.056 |

*Bovine serum albumin,
**Ovalbumin (2) Competitive ELISA

Figure 2:
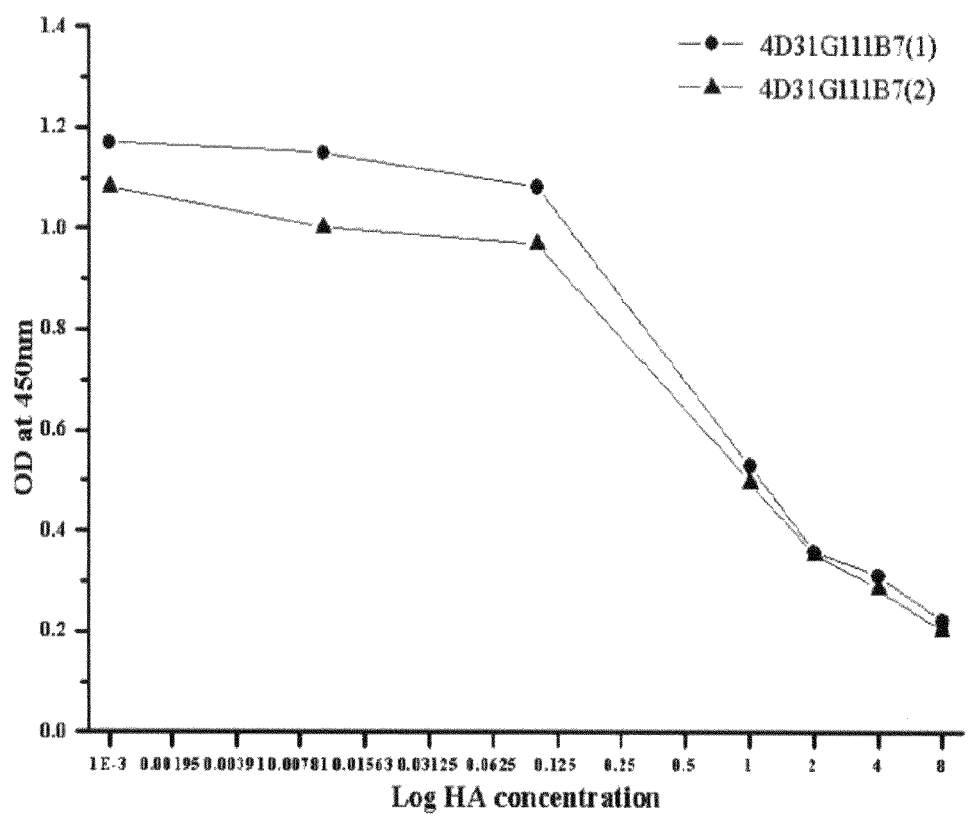
FIG. 2 is a graph showing the results of the competitive ELISA of purified monoclonal antibodies [4D31G111B7 (1) and (2)] for hippuric acid (HA)

Competitiveness and titer of the purified antibody 4D31G111B7 were determined by Competitive ELISA. OVA-HA as an assay conjugate was diluted to a concentration of 10 µg/mL in a 0.01 M carbonate buffer (pH 9.5), and was bound to an antigen in the same manner as in indirect ELISA. Constant concentrations of the antibody (ranging from 13.0 µg/mL to 1.62 µg/mL) and various concentrations of HA (ranging from 8 mg/mL to 0.001 g/mL) were mixed and reacted at 37° C. for 30 min. The resulting mixture was placed in a plate to which the OVA-HA conjugate was bound, and reacted again at 37° C. for 30 min. Subsequent procedures were the same as previously described in indirect ELISA (Pound, 1998). Color development with TMB substrate was carried out at room temperature for 5 min. Consequently, the ELISA-determined titers were 0.221 and 0.203 at the hippuric acid concentration of 8 mg/mL, and 1.276 and 1.212 in the absence of hippuric acid, and all cases exhibited a competition efficiency of more than 95% (see Table 3 and FIG. 2). Table 3 shows the results of competitive ELISA of purified monoclonal antibodies [4D31G111B7 (1) and (2)] for hippuric acid (HA). FIG. 2 graphically shows the above results.

TABLE 3

| HA (mg/ml) | 4D31G111B7(1) | 4D31G111B7(2) |
|---|---|---|
| 8 | 0.221 | 0.203 |
| 4 | 0.312 | 0.286 |
| 2 | 0.359 | 0.355 |
| 1 | 0.529 | 0.497 |
| 0.1 | 1.082 | 0.969 |
| 0.01 | 1.150 | 1.003 |
| 0.001 | 1.170 | 1.082 |
| 0 | 1.276 | 1.212 |

(3) Plot of Standard Curve

Figure 3:
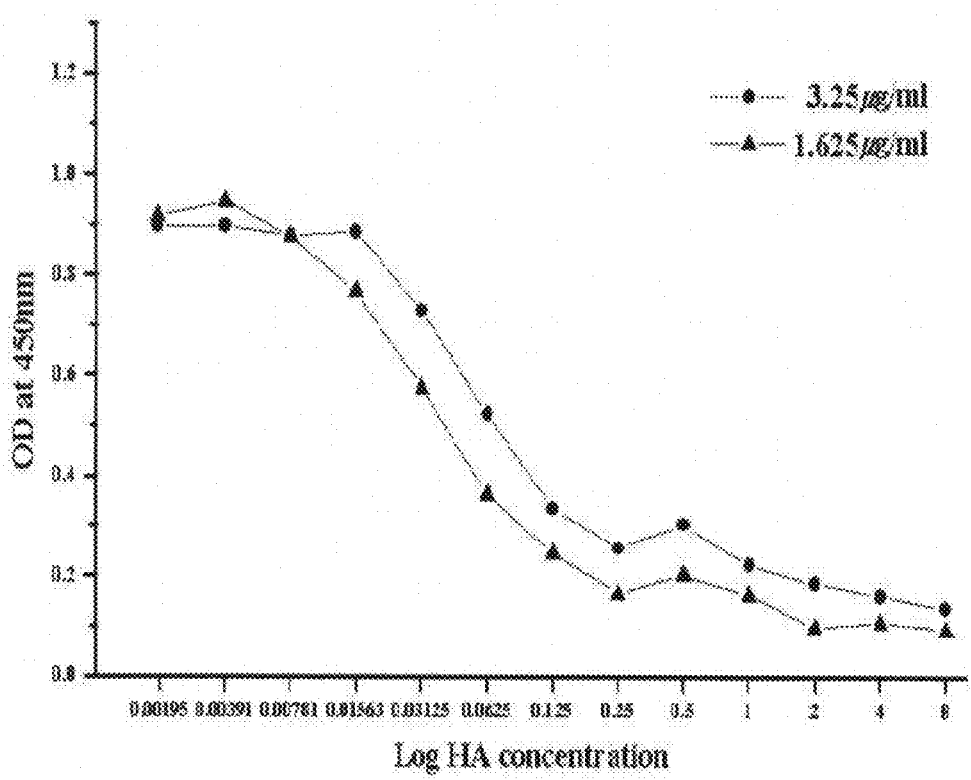
FIG. 3 is a graph showing the results of the competitive ELISA for various concentrations of HA (from 8 mg/mL to 0.0019 mg/mL) and the purified IgG (4D31G111B7) (3.25 µg/mL and 1.625 µg/mL)

A standard curve was plotted for the cell line 4D31G111B7 (2 µg/mL) versus HA concentrations (ranging from 0.5 mg/mL to 0.0078 mg/mL). An experimental method was carried out in the same manner as described above (Pound, 1998). This experiment was intended to examine at what concentrations the monoclonal antibody secreted by the established cell line (4D31G111B7) exhibits substantially high competition with an antibody directed against pure hippuric acid. Determination of competition therebetween was made by diluting the concentration of the monoclonal antibody at a 1/2-fold dilution ratio from 13 µg/mL to 1.625 µg/mL, and by diluting the concentration of hippuric acid at a 1/2-fold dilution ratio from 8 mg/mL to 0.001 mg/mL. As a result, the values obtained in the ranges of the monoclonal antibody concentration of 2.25 µg/mL and 1.625 µg/mL and the hippuric acid concentration of from 0.25 mg/mL to 0.0039 mg/mL displayed a linear curve, which are believed to be graph values capable of plotting the standard curve. According to the standard curve, the value of y=a+b x was y=(−0.1157)+(−0.5487)x, and $R^2$=0.983. Based on values of this graph, the concentration of hippuric acid in the test sample could be calculated by substitution of a concentration with a titer (see FIG. 3). FIG. 3 is a graph showing the results of competitive ELISA for various concentrations of HA (from 8 mg/mL to 0.0019 mg/mL) and purified IgG (4D31G111B7) (3.25 μg/mL and 1.625 μg/mL). Purified monoclonal antibodies were pre-incubated with HA at 37° C. for 30 min. The pre-incubation mixture was transferred to a well, pre-coated with an OVA-HA conjugate, and incubated at 37° C. for 30 min. Color development with TMB substrate was carried out at room temperature for 5 min. 3.25 μg/mL and 1.625 μg/mL concentrations of antibodies were allowed to compete with increasing concentrations of HA on the OVA-HA coated plates. The standard curve was determined in the region of HA concentration ranging from 0.25 mg/mL to 0.0156 mg/mL. When a linear standard curve is obtained in such a concentration region, it is possible to adjust the HA concentration to a cut-off concentration of 1 to 4 mg/mL which corresponds to the permissible exposure limit of toluene, by adjusting the amount of the monoclonal antibodies or the pH in a practical diagnostic kit.

Figure 4:
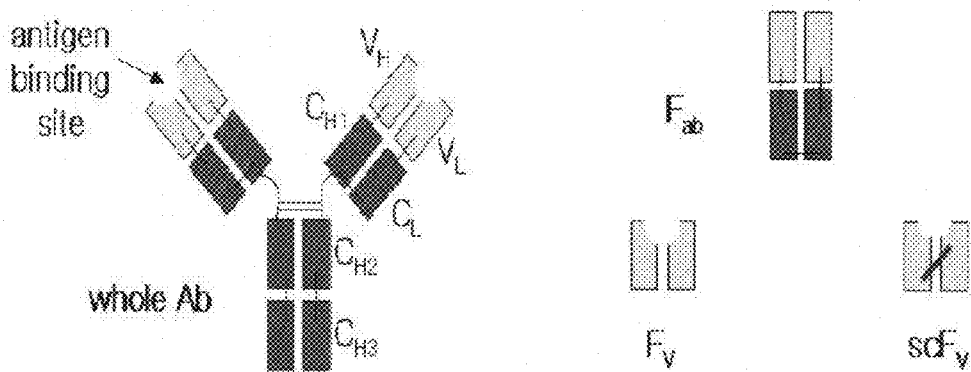
FIG. 4 shows a structure of an antibody (IgG) molecule and fragments thereof.

In order to determine the amino acid sequence of the monoclonal antibody secreted by the cell line 4D31G111B7 finally selected in previous Examples, the following experiments were carried out. FIG. 4 shows a structure of an antibody (IgG) molecule and fragments thereof. The IgG molecule consists of a heavy chain and a light chain, each of which being composed of variable domains (in light color) and constant domains (in dark color). The arrow in FIG. 4 represents an antigen-binding site. The Fab fragment may be prepared by papain treatment of the antibody, and the Fv fragment is the smallest antibody fragment that retains a complete antigen-binding site. scFv is a single-chain antibody, Fv domains of which are tethered together by a linker peptide. Since the constant domains are not sequences crucial to determination of antigen binding, the present invention has sequenced only the amino acid sequence of variable domains of the monoclonal antibody (4D31G111B7).

Example 8

Total RNA Isolation

The cell line 4D31G111B7 finally selected in previous Examples was sub-cultured in RPMI 1640 medium (Sigma, St Louis, USA), and the cultured cells were aliquoted into a fresh culture medium a day prior to total RNA isolation, such that cells can be maintained in healthy conditions. Isolation of the total RNA was carried out using Trizol (Sigma, USA). RNA was isolated from about $1\times10^7$ cells. Cells cultured in a T-flask were transferred to a plastic tube, and were then centrifuged at 150×g for 5 min. The supernatant was carefully decanted, and the pellets were re-suspended and transferred to a 1.5 mL tube. 1 mL of 0.1% DEPC was added thereto, and the resulting mixture was centrifuged at 4° C. and 150 ×g for 5 min. The supernatant was removed by pipetting. 1 mL of a trizol reagent was added to the pellets which were then completely re-suspended and subjected to lysis at room temperature for 5 min. 0.2 mL of chloroform was added to the lysis products, and the contents of the tube were intimately mixed for 15 sec and allowed to stand at room temperature for 3 min. Thereafter, out of three layers obtained after centrifugation at 4° C. (12,000×g, 15 min), a colorless top layer was carefully transferred to a fresh tube to which 0.5 mL of ice-cold isopropanol was then added, followed by standing it at room temperature for 10 min. Next, centrifugation (12,000×g, 10 min) was carried out at 4° C. to remove the supernatant, and the resulting RNA pellets were washed two times with 75% ethanol and dried in the air for about 10 min. Then, the thus-dried RNA pellets were dissolved in water treated with 30 μl of DEPC, and a portion of the thus-isolated total RNA was analyzed on 0.8% (w/v) agarose gel, thereby confirming 18S and 28S rRNA bands, and the remaining RNA was stored at a temperature of −20° C.

Example 9

Construction of PCR Primers

Diversity of antibodies is determined by amino acid sequences based upon any combination of numbers of genes (V, D and J) involved the expression of antibodies and is also additionally increased by other factors such as hypermutation. Therefore, in order to obtain variable regions of antibody heavy and light chains having unknown sequences, the first and most important thing is to construct a primer capable of covering as many sequences as possible. In fact, mice are known to show antibody diversity of maximum $1\times10^9$ to $10^{11}$. In order to meet more than 75% of such antibody diversity, 7 species of degenerated primers for the heavy chain, and 11 species of degenerated primers for the light chain, were used. Information for genes of mouse immunoglobulin heavy chain (gamma 1) and light chain (kappa chain), listed in IMGT bank (The International ImMunoGeneTics database: http://www.imgt.cines.fr:8104), was acquired and the DNA base sequence of the constant region was selected. Based on these data, anti-sense primers for heavy and light chains, and forward primers (primers MKV75 and MHV78) coding for the variable region FRI, which were previously studied by S. Essono et al (2003), were constructed by Bioneer (Daejeon, Korea). In addition, for recombination of a desired gene into an expression vector, the 5'-MHV78 forward primer was designed to have a recognition site of the restriction enzyme Sfl I, whereas the 3'-MKC anti-sense primer was provided with a recognition site of the restriction enzyme Not I. In order to form the single chain variable fragment (ScFv), a flexible linker DNA encoding the peptide $(Gly_4Ser)_3$, which connects the heavy chain to the light chain (kappa chain), was constructed by Bioneer (Daejeon, Korea). DNA sequences of backward primers (SEQ ID NOS: 10-11) and forward primers (SEQ ID NOS: 12-29) used in RT-PCR experiment of the present invention are respectively set forth in Tables 4a and 4b below.

TABLE 4a

DNA sequences of backward primers

| Primer Name | Sequence |
|---|---|
| Heavy chain backward primer (SEQ ID NO: 10) | 5'-AGGGGCCAGTGGATAGACNGATGG-3' |
| Kappa chain backward primer (SEQ ID NO: 11) | 5'-ACCTGCGGCCGCTACAGTTGGTGCAGCATCAGC-3' |

* Note: N = A/G/C/T

TABLE 4b

DNA sequences of forward primers

| Primer Name | Sequence |
|---|---|
| MHV78 forward primer 1 (SEQ ID NO: 12) | 5'-GCGGCCCAGCCGGCCSAGGTCCAGCAGCTGCAGYYTGG-3' |
| MHV78 forward primer 2 (SEQ ID NO: 13) | 5'-GCGGCCCAGCCGGCCCAGGTRCAGCTGAAGSAGTCAGG-3' |
| MHV78 forward primer 3 (SEQ ID NO: 14) | 5'-GCGGCCCAGCCGGCCGAKGTGCAGCTTCAGCAGTCRGG-3' |
| MHV78 forward primer 4 (SEQ ID NO: 15) | 5'-GCGGCCCAGCCGGCCGAVGTGAWGCTGGTGGAGTCTGR-3' |
| MHV78 forward primer 5 (SEQ ID NO: 16) | 5'-GCGGCCCAGCCGGCCGAAGTGCAGCTGTTGGAGACTGG-3' |
| MHV78 forward primer 6 (SEQ ID NO: 17) | 5'-GCGGCCCAGCCGGCCGAGGTTVAGVTGCAGCAGTCTGK-3' |
| MHV78 forward primer 7 (SEQ ID NO: 18) | 5'-GCGGCCCAGCCGGCCCAGGTTCACCTACAACAGTCTGG-3' |
| MKV75 forward primer 1 (SEQ ID NO: 19) | 5'-CTCTGGCGGTGGCGGATCGGATGYTKTKVTGACCCAAACTCC-3' |
| MKV75 forward primer 2 (SEQ ID NO: 20) | 5'-CTCTGGCGGTGGCGGATCGRACATTGTGCTGACMCAATCTCC-3' |
| MKV75 forward primer 3 (SEQ ID NO: 21) | 5'-CTCTGGCGGTGGCGGATCGSAAAWTGTKCTCWCCCAGTCTCC-3' |
| MKV75 forward primer 4 (SEQ ID NO: 22) | 5'-CTCTGGCGGTGGCGGATCGSAAAWTCTKCTCWCCCAGTCTCC-3' |
| MKV75 forward primer 5 (SEQ ID NO: 23) | 5'-CTCTGGCGGTGGCGGATCGSAAAWTTTKCTCWCCCAGTCTCC-3' |
| MKV75 forward primer 6 (SEQ ID NO: 24) | 5'-CTCTGGCGGTGGCGGATCGARCATTGTGATGACCCAGWCTCA-3' |
| MKV75 forward primer 7 (SEQ ID NO: 25) | 5'-CTCTGGCGGTGGCGGATCGARCATTGTGATGACCCAGWCTCC-3' |
| MKV75 forward primer 8 (SEQ ID NO: 26) | 5'-CTCTGGCGGTGGCGGATCGGRCATTGTGATGACCCAGWCTCA-3' |
| MKV75 forward primer 9 (SEQ ID NO: 27) | 5'-CTCTGGCGGTGGCGGATCGGRCATTGTGATGACCCAGWCTCC-3' |
| MKV75 forward primer 10 (SEQ ID NO: 28) | 5'-CTCTGGCGGTGGCGGATCGGATATCCAGATGACACAGACTAC-3' |
| MKV75 forward primer 11 (SEQ ID NO: 29) | 5'-CTCTGGCGGTGGCGGATCGGAMATCMWGATGACCCARTCTCC-3' |

* R = A/G; Y = C/T; M = A/C; K = G/T; S = C/G; W = A/T; H = A/C/T; B = C/G/T; V = A/C/G; D = A/G/T.

Example 10

Amplification of Heavy- and Light-Chain Variable Regions (RT-PCR)

RT-PCR was carried out using BD SMART™ RACE Amplification Kit (BD Biosciences Clontech, USA). More than 1 µg of the total RNA and each 10 pmol/µl of anti-sense primers for the heavy chain (SEQ ID NO: 10) and the light kappa chain (SEQ ID NO: 11) were mixed, allowed to stand at 70° C. for 2 min and placed on ice for 2 min. 1 µl of 5× First-strand buffer, 2 mM DTT, 1 mM dNTP mix and BD PowerScript Reverse Transcriptase were mixed. RNA, previously reacted at 70° C., was added to the resulting mixture which was then reacted in an incubator at 42° C. for 90 min. After reaction was complete, 100 µl of Tricine-EDTA buffer was added to the reaction mixture which was then reacted at 72° C. for 7 min. Immediately thereafter, a PCR process was carried out, and the remaining parts were stored at −20° C.

For a 50 µl total volume PCR reaction, 5 µl cDNA product, 10× PCR buffer (100 mM Tris-HCl, 15 mM MgCl$_2$, and 50 mM KCl, pH 8.3), 1 pmol/µl primer set, 0.2 mM dNTPs, 1 mM MgCl$_2$, and 5 units of Taq DNA polymerase were introduced into a reaction vessel and a final volume of a reaction mixture was adjusted by sterile triple-distilled water. The PCR reaction of the heavy chain consisted of 35 cycles, each cycle including: heating to denature DNA at 94° C. for 5 min (pre-denaturation), 94° C. for 30 sec (denaturation), 55° C. for 30 sec (annealing) and 72° C. for 30 sec (polymerization). After the final cycle, the PCR reaction was terminated by heating at 72° C. for another 10 min. The PCR reaction of the light chain consisted of 35 cycles, each cycle including: heating DNA at 94° C. for 5 min (pre-denaturation), 94° C. for 30 sec (denaturation), 51° C. for 30 sec (annealing) and 72° C. for 30 sec (polymerization). After the final cycle, the PCR reaction was terminated by heating at 72° C. for another 10 min. A portion of the PCR products was subjected to electrophoresis on 1.2% agarose gel made up of 1× TAE buffer (40 mM Tris-acetate, 1 mM EDTA), and stained with ethidium bromide (0.5 µg/mL) to confirm amplification of genes.

was adjusted to 50 µl by sterile triple-distilled water, which was then homogeneously mixed and added to the previously-performed PCR reaction. The PCR reaction consisted of 35 cycles, each cycle including: heat treatment at 94° C. for 5 min (pre-denaturation), 94° C. for 30 sec (denaturation), 59° C. for 30 sec (annealing) and 72° C. for 50 sec (polymerization). After the final cycle, the PCR reaction was terminated by heating at 72° C. for another 10 min. The sequence of the linker DNA (SEQ ID NO: 30) used in assembly of the scFv gene is set forth in Table 5.

TABLE 5

| Linker Name | Sequence |
| --- | --- |
| linker DNA (SEQ ID NO: 30) | 5'-CGATCCGCCACCGCCAGAGCCACCTCCGCCTGAACCGCCTCCACCAGGGGCCAGTGGATAGAC-3' |

Figure 5:
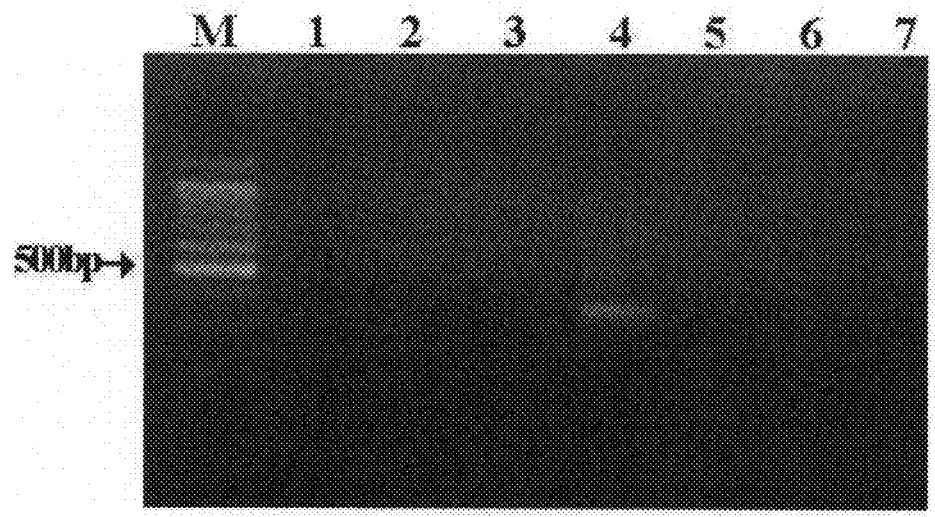
FIG. 5 is a photograph showing agarose gel electrophoresis patterns of the PCR amplification products of hybridoma cDNA, using 7 species of MHV 78 primers.
Figure 6:
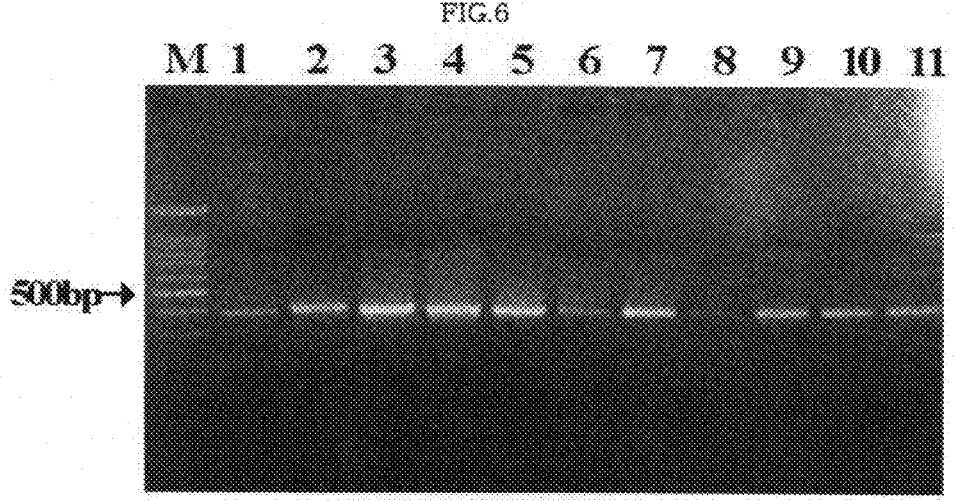
FIG. 6 is a photograph showing agarose gel electrophoresis patterns of the PCR amplification products of hybridoma cDNA, using 11 species of MKV 75 primers.

Using reverse transcriptase, cDNAs were synthesized from the total RNA as a template. PCR reaction using the thus-synthesized cDNAs as a template employed 7 degenerated primers capable of representing about 78% of the mouse heavy chain variable region (SEQ ID NOS: 12-18), and 11 degenerated primers capable of representing about 75% of the mouse light chain variable region (SEQ ID NOS: 19-29) (see Table 4). The resultant PCR products were analyzed on 1.2% agarose gel. The heavy chain exhibited a band at a place where the 4th primer was used (see FIG. 5), whereas the light chain exhibited bands for all primers (FIG. 6). These results are believed to be due to the use of degenerated primers as the primer sequences, and high similarity in sequences therebetween. The most conspicuous third primer was selected for subsequent experiments. The heavy chain and light kappa chain exhibited bands at sizes of 320 bps and 340 bps, respectively (see FIGS. 5 and 6). FIG. 5 is a photograph showing agarose gel electrophoresis patterns of PCR amplification products of hybridoma cDNA, using 7 species of MHV 78 primers (SEQ ID NOS: 12-18). In FIG. 5, Lane M represents a 100 bp DNA ladder, and Lanes 1 through 7 represent PCR products of the heavy chain variable region gene. FIG. 6 is a photograph showing agarose gel electrophoresis patterns of PCR amplification products of hybridoma cDNA, using 11 species of MKV 75 primers (SEQ ID NOS: 19-29). In FIG. 6, Lane M represents a 100 bp DNA ladder, and Lanes 1 through 11 represent PCR products of the light chain (kappa chain) variable region gene.

Example 11

Assembly of Single Chain Variable Fragment (ScFv)

Figure 7:
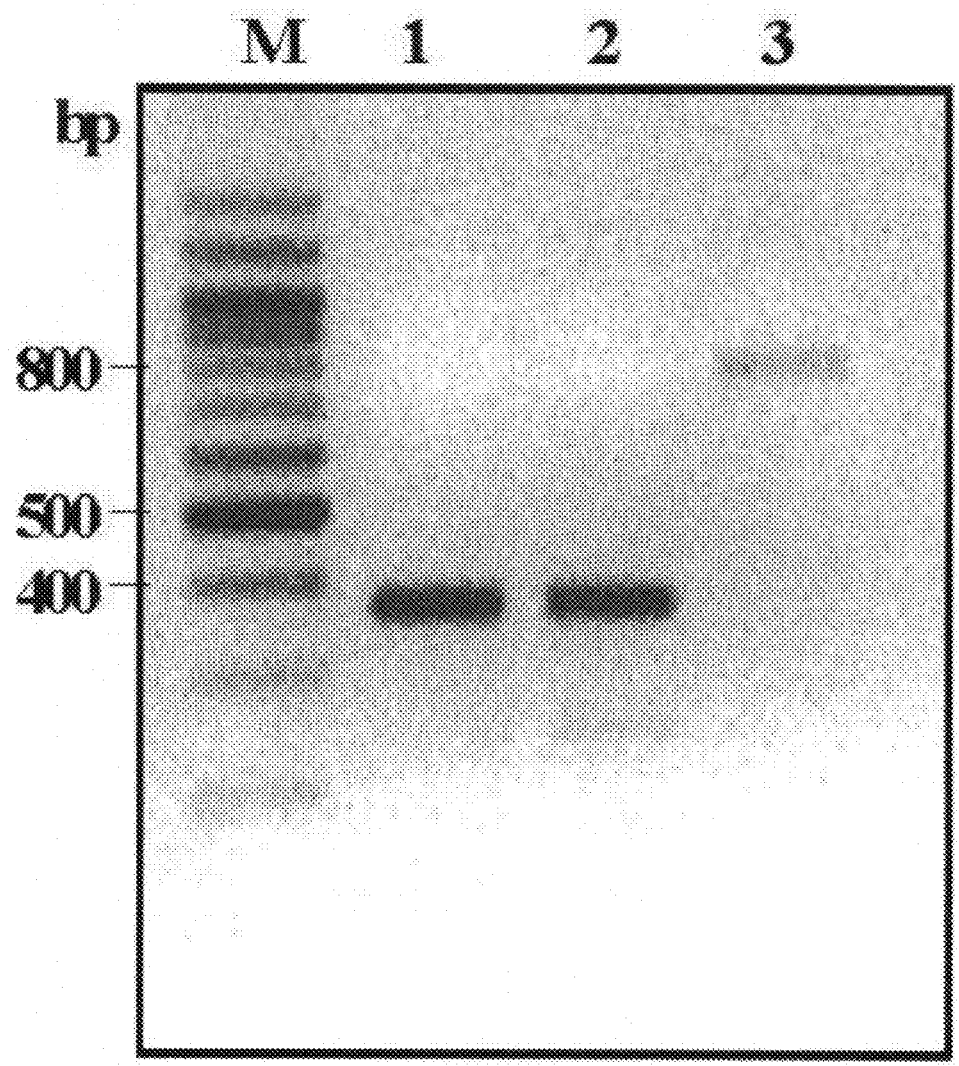
FIG. 7 is a photograph showing agarose gel electrophoresis patterns of the PCR amplification products of $V_H$, $V_K$ and scFv.

For recombination of PCR products into an expression vector, all of the PCR products were electrophoresed on 1.2% agarose gel. The gel was placed on a UV illuminator, and the precisely amplified DNA band was cut out using a razor blade. Then, DNA was separated and purified from the gel, using Geneclean III kit (BIO101, USA). The PCR products of the heavy chain and light chain were assembled into a single polypeptide by Splicing by Overlap Extension PCR (SOE-PCR) (Horton et al., 1989). ScFv was assembled in two steps. In a first step, 50 ng of each purified PCR product and 40 pmol of a linker DNA (SEQ ID NO: 30), 10× PCR buffer (100 mM Tris-HCl, 15 mM $MgCl_2$, and 50 mM KCl, pH 8.3), 0.2 mM dNTPs, 1 mM $MgCl_2$ and 5 units of Taq DNA polymerase were introduced into a reaction vessel, and the final volume Two PCR-amplified genes were separated and purified, and linked together to form a single gene via a linker DNA composed of Gly and Ser. Using SOE-PCR, the thus-formed single gene was amplified in two steps. From the results of analysis on 1.2% agarose gel, it was confirmed that a product consisting of about 800 bps in length was formed (see FIG. 7). FIG. 7 is a photograph showing agarose gel electrophoresis patterns of PCR amplification products of $V_H$, $V_K$ and scFv. Lane M represents a 100 bp DNA ladder. $V_H$ gene was amplified using a heavy chain backward primer and MHV78 forward primer 4 (Lane 1). $V_K$ gene was amplified using a light chain backward primer and MKV75 forward primer 3 (Lane 2). Lane 3 represents the assembled scFv gene. $V_H$ gene and $V_K$ gene were connected via a linker DNA to form scFv by SOE-PCR.

Example 12

Recombination of PCR Product into Cloning Vector

Figure 8:
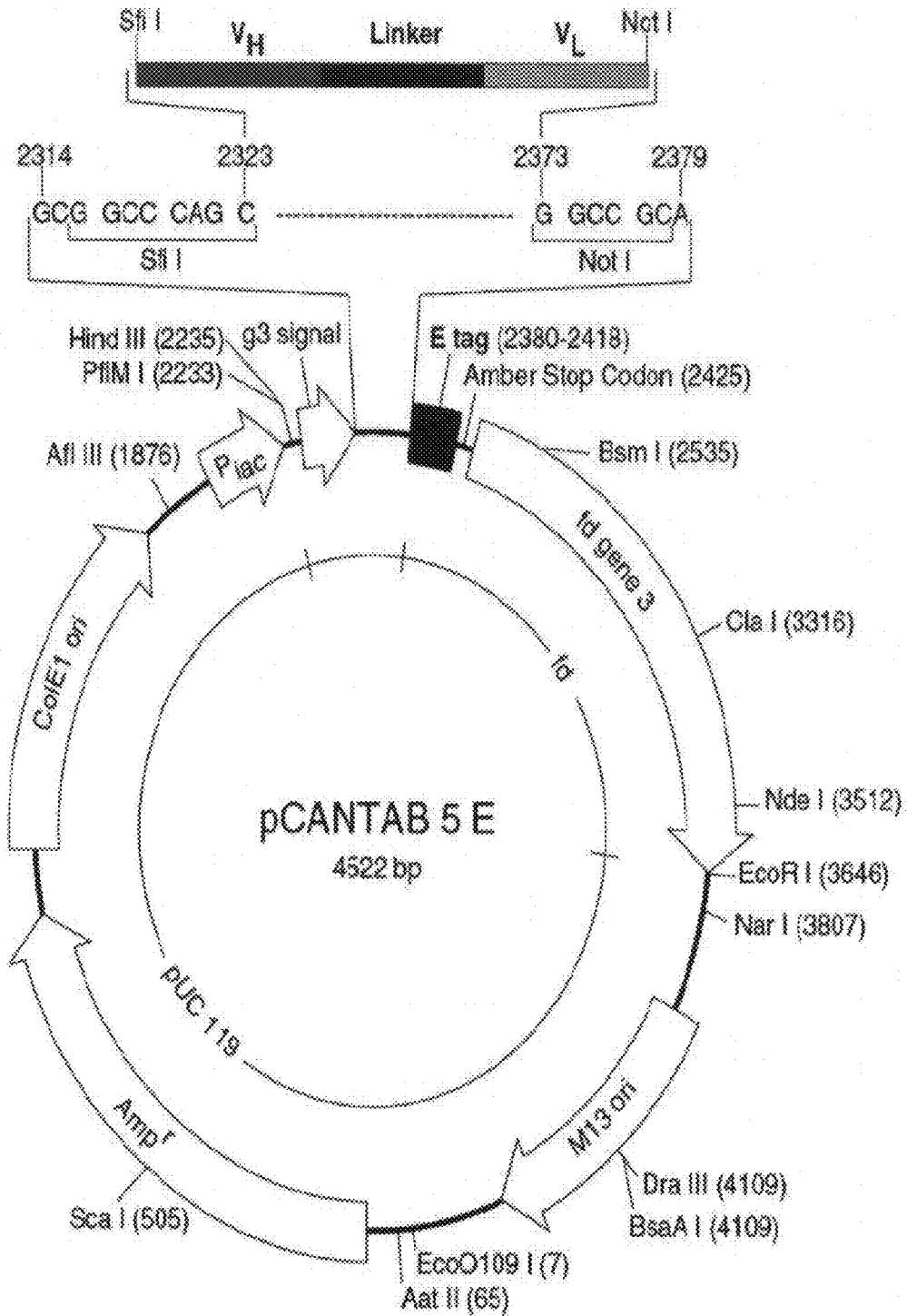
FIG. 8 is a map of an expression vector pCANTAB5E.

For recombination of the PCR product extracted as above, the PCR product was treated with restriction enzymes Sfi I and Not I, respectively, and the-thus treated PCR product was purified using Geneclean III kit (BIO101, USA). As a cloning vector, Phagemid pCANTAB5E (Amersham Biosciences, Sweden) vector was used. This vector is designed such that the antibody variable region genes can be cloned between the leader sequence and the main body of the M13 gene. pCANTAB5E also contains a sequence coding for a peptide tag (E tag) followed by an amber stop codon. Therefore, when a supE strain of E. coli such as TG1 is present, translation continues through the amber stop codon to produce the ScFv-g3p fusion protein. Whereas, in nonsuppressor strains such as HB2151 (Amersham Biosciences, Sweden), the stop codon is recognized, protein synthesis is aborted at the end of the ScFv gene, and g3p fusion protein is not synthesized. FIG. 8 is a map of an expression vector pCANTAB5E. If the expression vector pCANTAB5E has the amber translational stop codon at the junction between the cloned scFv and the g3p sequence, this vector contains a peptide E tag-coding sequence before the amber translational stop codon.

The PCR product, purified after treatment with restriction enzymes, and the pCANTAB5E vector were mixed in a ratio of 3:1, and 1 µl of 10× ligation buffer (0.66 M Tris-HCl, pH 7.6, 50 mM $MgCl_2$, and 50 mM dithiothreitol), 10 mM ATP, and 1 unit of T4 DNA ligase were added to the resulting mixture, followed by overnight reaction at 4° C., thus completing recombination.

Example 13

Transformation

For transformation of the recombination product obtained as above, competent cells of *E. coli* JM109 were prepared and used for transformation. 200 μl of the competent cells stored at −70° C. was slowly thawed on ice, and 10 μl of the recombination reaction product was added to the thawed cells, followed by standing of the reaction mixture on ice for 30 min. Heat shock was applied to the reaction mixture at 42° C. for 90 sec and the mixture was again allowed to stand on ice for 10 min. Then, 800 μl of SOC (2% Bacto-tryptone, 0.5% Bacto-yeast extract, 10 mM NaCl, 2.5 mM KCl, 10 mM MgSO$_4$, 10 mM MgCl$_2$ and 20 mM glucose) was added to the mixture which was then cultured at 37° C. for 1 hour. Next, 100 μl of the resulting culture was spread on SOB plating medium containing ampicillin (100 μg/mL) and 2% glucose and was cultured at 37° C. for 12 to 16 hours. Here, several ones among the formed colonies were picked and re-cultured in 2×YT-AG medium (17 g of Bacto-tryptone, 10 g of Bacto-yeast extract, 5 g of NaCl, 100 μg/mL of ampicillin, and 2% glucose) to confirm the insertion of the recombination product.

Example 14

Cloning Confirmation and Sequencing by PCR

From the transformant constructed in Example 14, a plasmid was extracted using alkaline lysis (Sambrook & Russell, 1989). The presence of the inserted DNA was confirmed via PCR reaction using the extracted plasmid as a template. The PCR reaction was carried out using the recombinant plasmid and 10×PCR buffer (100 mM Tris-HCl, 15 mM MgCl$_2$, and 50 mM KCl, pH 8.3), 10 pmol/μl heavy chain forward primer and 10 pmol/μl kappa chain anti-sense primer, 0.2 mM dNTPs, and 5 units of Taq DNA polymerase (Promega, USA). The PCR reaction consisted of 35 cycles, each cycle including: reacting to sufficiently denature DNA at 94° C. for 5 min, 94° C. for 30 sec (denaturation), 59° C. for 30 sec (annealing), and 72° C. for 50 sec (polymerization). After the final cycle, the PCR reaction was terminated by heating at 72° C. for another 10 min. After the PCR reaction was complete, a portion of the reaction products was subjected to electrophoresis on 1.2% agarose gel made up of 1× TAE buffer (40 mM Tris-acetate, 1 mM EDTA), and stained with ethidium bromide (0.5 μg/mL) to confirm amplification of genes.

Figure 9:
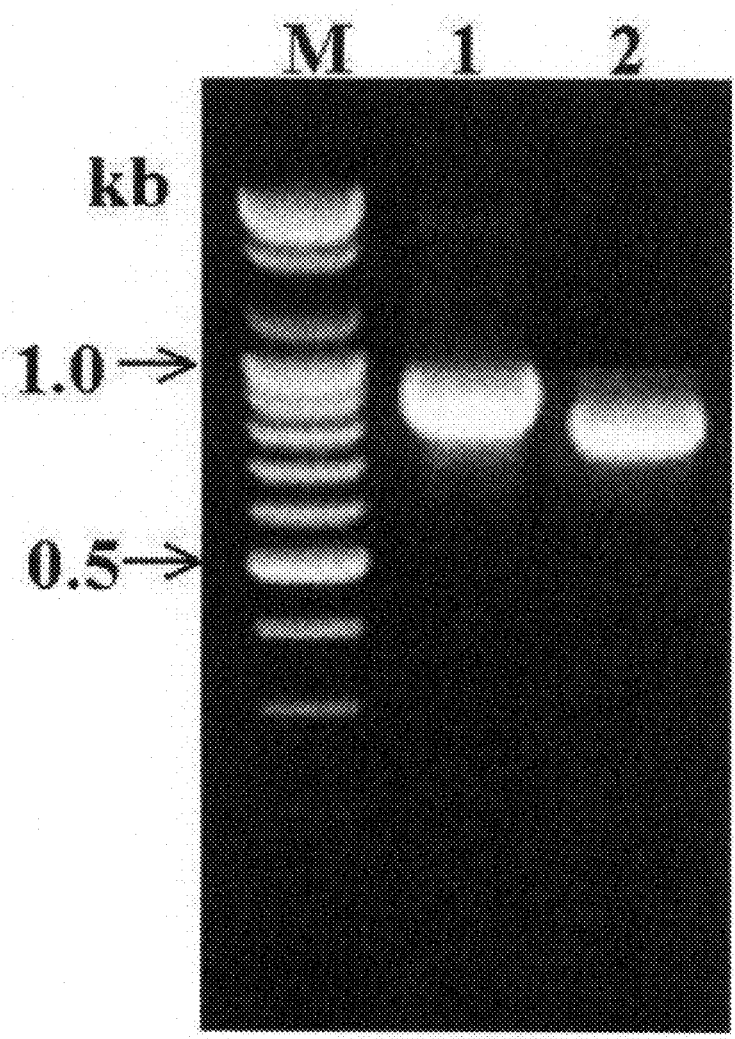
FIG. 9 is an electrophoresis photograph confirming the cloning of scFv into pCNATAB5E via PCR.

An 800 bp DNA fragment was cloned into the expression vector pCANTAB5E (Amersham Biosciences, Sweden) which was then transformed into *E. coli* JM109. After primary selection of colonies with an antibiotic, phagemids were extracted from the selected colonies, and the desired colonies were identified and compared through the PCR reaction using a heavy chain forward primer, a light chain anti-sense primer and a sequencing primer set (S1, S6) (see FIG. 9). The base sequence of the sequencing primer set (S1, S6) used herein is set forth in Table 6 below. FIG. 9 is an electrophoresis photograph confirming the cloning of scFv into pCNATAB5E by PCR, wherein Lane M represents a 1 kb PLUS DNA ladder, Lane 1 represents a PCR product using pCANTAB5 sequence primers 1(SEQ ID NO: 31) and 6(SEQ ID NO: 32), and Lane 2 represents a PCR product using an MHV78 forward primer (SEQ ID NOS: 12-18) and a kappa chain backward primer (SEQ ID NO: 11).

TABLE 6

| Primer Name | Sequence |
|---|---|
| Sequencing primer 1 (SEQ ID NO: 31) | 5'-CAACGTGAAAAAATTATTATTCGC-3' |
| Sequencing primer 6 (SEQ ID NO: 32) | 5'-CATTTACTTAAAAGACATACTCC-3' |

The phagemids were re-extracted from the colonies in which insertions were confirmed and were DNA-sequenced by Genotech (Daejeon, Korea) using ABI PRISM 3700 DNA Analyzer. Upon DNA sequencing of scFv, V$_H$ consisting of 321 bps and V$_L$ consisting of 324 bps could be confirmed, and DNA sequences of the linker DNA and E-tag were identified in intact forms (see FIG. 10). Further, the amino acid sequence of scFv is set forth in SEQ. ID. NO: 9. The amino acid composition of scFv and the regions assigned into CDRs and FRs were analyzed using IMGT/V-QUEST database (http://imgt.cines.fr) which is a sequence alignment software for the immunoglobulin and is freely accessible via the Internet (see FIG. 11). CDRs (complementarity determining regions), which structurally constitute antigen-binding sites within variable regions of the monoclonal antibody, are important parts determining specific complementarity with an antigen of interest. FIG. 10 shows a base sequence and a deduced amino acid sequence of the scFv gene. FIG. 11 shows amino acid sequences of variable regions (V$_H$ and V$_K$) Of heavy chain and light chain (kappa chain) deduced from scFv. CDRs and FRs are indicated in FIG. 11. Throughout the present specification, the amino acid sequences of CDR1, 2 and 3 of the heavy chain variable region (SEQ. ID. NO: 4) are set forth in SEQ. ID. NO: 1, SEQ. ID. NO: 2 and SEQ. ID. NO: 3, respectively. The amino acid sequences of CDR1, 2 and 3 of the light chain variable region (SEQ. ID. NO: 8) are set forth in SEQ. ID. NO: 5, SEQ. ID. NO: 6 and SEQ. ID. NO: 7, respectively.

Example 15

Expression of Proteins

For expression of the recombinant plasmid whose base sequence was identified, the recombinant plasmid was transformed into *E. coli* HB2151. Preparation and transformation of the competent cell of *E. coli* HB2151 were carried out in the same manner as in the method for *E. coli* JM109 described hereinbefore. After selection of the recombinant plasmid-transformed colonies and induction of expression thereof with IPTG, expression of desired proteins was confirmed by Sodium Dodecyl Sulfate-Polyacrylamide Gel Electrophoresis (SDS-PAGE). Further, in order to locate the position of the soluble ScFv-E tag expressed in *E. coli* HB2151, Western blot analysis was carried out using a mouse anti-E tag antibody. The above expression-induced soluble ScFv-E tag was dissolved and separated by 12% SDS-PAGE, and transferred onto NitroCellulose (NC) membrane using Trans-Blot SD semi-dry transfer (BioRAD, USA) at 26 V for 35 min. A NitroCellulose (NC) membrane was cut into an appropriate size, and was previously soaked in conjunction with a pad in the transfer buffer for subsequent use. After transfer was complete, the membrane was blocked in a blocking solution (5% skim milk) at 4° C. for 12 hours. When membrane blocking was complete, the membrane was treated at 37° C. for 1 hour with a solution in which the mouse anti-E tag antibody was diluted to 1:500 in the blocking solution. Then, goat anti-mouse IgG-HRP (horseradish peroxide) (KBL, USA) was diluted to 1:5,000 and treated on the membrane at 37° C. for 1 hour. Prior to performing each treatment step, the membrane was washed three times for 5 min each with phosphate buffered saline (PBST) to which a 0.05% (w/v) Tween 20 solution was added. For color development, 20 mg of 3,3'-diaminobenzidine (DAB, Sigma, USA) as a substrate of HRP and 0.015% hydrogen peroxide were mixed in 50 mL of PBS, and the membrane was then soaked in the resulting solution and reacted under gentle stirring to observe the results of color development. FIG. 12 is a photograph showing the results of SDS-PAGE and Western blot analysis of scFv expression, wherein Lane M represents a protein size marker II (Tefco, Japan), Lane 1 represents the supernatant of *E. coli* HB2151, Lane 2 represents the supernatant of non-IPTG-induced, cloned *E. coli* HB2151 cells, and Lane 3 represents the supernatant of cloned *E. coli* HB2151 cells, harvested 9 hours after induction with IPTG. The expressed scFv-E tag is indicated by an arrow.

Example 16

Isolation and Purification of Expressed Proteins

For this Example, RPAS Purification Module was purchased and used to isolate and purify ScFv-E tag. First, *E. coli* HB2151 strain was inoculated into 1 L of 2×YT-A liquid medium and grown to $OD_{600}$ of 0.5 to 0.6. 1 mM of IPTG was added to the culture medium, and expression was induced for 5 hours, followed by standing it on ice for 5 min to terminate protein expression. 1 L of the resulting culture was centrifuged at 1,500×g and the supernatant was discarded. The resulting pellets were dissolved in an extraction buffer and subjected to 12% SDS-PAGE to confirm whether desired proteins were expressed. The remaining portion of the cell culture was dialyzed four times against PBS at 4° C. for 3 hours each, thereby performing replacement of buffer solutions. scFv-E tag was isolated using HiTrap™ anti-E tag column and AKTA purifier 10 (Amersham Biosciences, Sweden). The column was equilibrated by washing with 0.2 M phosphate buffer, and the dialyzed sample was added to bind with antibodies. Thereafter, the column was washed with the same 0.2 M phosphate buffer to remove proteins not bound to anti-E tag, and the bound scFv-E tag was eluted with 1.0 M Glycine buffer (pH 3.0). A 1M Tris-HCl buffer (pH 8.0) was added to the thus-eluted sample in an amount corresponding to 1/10 volume of the eluate, thereby returning the pH value of the sample to an initial value. Using 100-fold volume of PBS, the eluted sample was dialyzed four times against PBS at 4° C. for 3 hours each, thereby performing replacement of buffer solutions. Using the indirect ELISA method as described hereinbefore, the reactivity of the thus-purified soluble scFv-E tag with a hippuric acid antigen was determined. Rabbit anti-E tag antibody and goat anti-rabbit IgG-HRP were employed as secondary antibodies. Upon performing indirect ELISA to determine the reactivity between the expressed protein scFv and hippuric acid antigen, the antibody titer of 0.516 was determined at 10-fold dilution (data not shown).

INDUSTRIAL APPLICABILITY

The monoclonal antibody screened according to the present invention has a titer having a standard curve in the concentration range of mg/mL meeting requirements for permissible exposure limit (PEL) of toluene, exhibits no cross-reactivity with a carrier protein, exhibits higher competitive inhibition in response to an increasing concentration of hippuric acid and exhibits no cross-reactivity with other proteins contained in the urine, and therefore can be usefully employed in a diagnostic kit for detection of hippuric acid which is capable of diagnosing toluene exposure. Therefore, the monoclonal antibody of the present invention can be used to confirm the exposure of worker groups or the like to hazardous environmental factors under working conditions, such as toluene, and to prevent and inhibit drug misuse and abuse of student groups or soldier groups.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A monoclonal antibody against a hippuric acid antigen, comprising:
   a heavy chain variable region having a CDR1 region with the amino acid sequence of SEQ ID NO: 1, a CDR2 region with the amino acid sequence of SEQ ID NO: 2, and a CDR3 region with the amino acid sequence of SEQ ID NO: 3; and
   a light chain variable region having a CDR1 region with the amino acid sequence of SEQ ID NO: 5, a CDR2 region having the amino acid sequence of SEQ ID NO: 6, and a CDR3 region having the amino acid sequence of SEQ ID NO: 7.

2. The monoclonal antibody according to claim 1, wherein the monoclonal antibody is a single chain variable fragment (scFv), and wherein the heavy chain variable region and the light chain variable region are linked by a peptide linker.

3. The monoclonal antibody according to claim 2, wherein the single chain variable fragment (scFv) includes the amino acid sequence of SEQ ID NO: 9.

* * * * *

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: CDR1 of VH

<400> SEQUENCE: 1

Gly Tyr Ser Phe Thr Gly Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 of VH
```

```
<400> SEQUENCE: 2

Ile Thr Pro Tyr Asn Gly Ala Thr
1               5

<210> SEQ ID NO 3
<211> LENGTH: 7
<212> TYPE: PRT
<213> ORGANISM: Artificial Sequence
<220> FEATURE:
<223> OTHER INFORMATION: CDR3 of VH

<400> SEQUENCE: 3

Val Arg Met Tyr Ala Asp Val
1               5

<210> SEQ ID NO 4
<211> LENGTH: 120
<212> TYPE: PRT
<213> ORGANISM: Artificial Sequence
<220> FEATURE:
<223> OTHER INFORMATION: VH

<400> SEQUENCE: 4

Glu Val Met Leu Val Glu Ser Gly Ala Ser Val Lys Ile Ser Cys Lys
1               5                   10                  15

Ala Ser Gly Tyr Ser Phe Thr Gly Tyr Tyr Met His Trp Val Lys Gln
                20                  25                  30

Ser His Val Lys Thr Leu Glu Trp Val Gly Arg Ile Thr Pro Tyr Asn
            35                  40                  45

Gly Ala Thr Asn Tyr Thr Gln Asn Phe Lys Lys Ala Ser Leu Thr
        50                  55                  60

Val Asp Lys Ser Ser Ser Thr Ala Tyr Met Glu Phe His Ser Leu Thr
65                  70                  75                  80

Ser Glu Asp Ser Ala Val Tyr Tyr Cys Val Arg Met Tyr Ala Asp Val
                85                  90                  95

Trp Gly Ala Gly Thr Ser Val Thr Val Ser Ser Val Lys Thr Thr Pro
            100                 105                 110

Pro Ser Val Tyr Pro Leu Ala Pro
        115                 120

<210> SEQ ID NO 5
<211> LENGTH: 11
<212> TYPE: PRT
<213> ORGANISM: Artificial Sequence
<220> FEATURE:
<223> OTHER INFORMATION: CDR1 of VL

<400> SEQUENCE: 5

Gly Ala Ser Gln Asp Ile Gly Gly Arg Leu Asn
1               5                   10

<210> SEQ ID NO 6
<211> LENGTH: 6
<212> TYPE: PRT
<213> ORGANISM: Artificial Sequence
<220> FEATURE:
<223> OTHER INFORMATION: CDR2 of VL

<400> SEQUENCE: 6

Ala Thr Ser Ser Leu Asp
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: CDR3 of VL

<400> SEQUENCE: 7

Leu Gln Tyr Asp Arg Ser Pro Tyr Thr
1               5

<210> SEQ ID NO 8
<211> LENGTH: 116
<212> TYPE: PRT
<213> ORGANISM: Artificial Sequence
<220> FEATURE:
<223> OTHER INFORMATION: VL

<400> SEQUENCE: 8

Glu Leu Val Leu Thr Gln Ser Pro Ser Ser Leu Ser Ala Ser Leu Gly
1               5                   10                  15

Glu Ser Val Thr Leu Ala Cys Arg Gly Ala Ser Gln Asp Ile Gly Gly
                20                  25                  30

Arg Leu Asn Trp Leu Gln Gln Glu Ala Asp Gly Thr Ile Lys Arg Leu
            35                  40                  45

Ile Tyr Ala Thr Ser Ser Leu Asp Ser Gly Val Pro Lys Arg Phe Ser
    50                  55                  60

Gly Arg Ser Gly Asp Tyr Ser Leu Thr Ile Ser Ser Leu Glu Ser
65                  70                  75                  80

Glu Asp Phe Val Asp Asp Tyr Tyr Cys Leu Gln Tyr Asp Arg Ser Pro
                85                  90                  95

Tyr Thr Phe Gly Gly Gly Thr Lys Leu Glu Ile Lys Arg Gly Asp Ala
            100                 105                 110

Ala Pro Thr Val
            115

<210> SEQ ID NO 9
<211> LENGTH: 258
<212> TYPE: PRT
<213> ORGANISM: Artificial Sequence
<220> FEATURE:
<223> OTHER INFORMATION: scFv

<400> SEQUENCE: 9

Ala Ala Gln Pro Ala Glu Val Met Leu Val Glu Ser Gly Ala Ser Val
1               5                   10                  15

Lys Ile Ser Cys Lys Ala Ser Gly Tyr Ser Phe Thr Gly Tyr Tyr Met
                20                  25                  30

His Trp Val Lys Gln Ser His Val Lys Thr Leu Glu Trp Val Gly Arg
            35                  40                  45

Ile Thr Pro Tyr Asn Gly Ala Thr Asn Tyr Asn Gln Asn Phe Lys Asp
    50                  55                  60

Lys Ala Ser Leu Thr Val Asp Lys Ser Ser Thr Ala Tyr Met Glu
65                  70                  75                  80

Phe His Ser Leu Thr Ser Glu Asp Ser Ala Val Tyr Tyr Cys Val Arg
                85                  90                  95

Met Tyr Ala Asp Val Trp Gly Ala Gly Thr Ser Val Thr Val Ser Ser
            100                 105                 110

Val Lys Thr Thr Pro Pro Ser Val Tyr Pro Leu Ala Pro Gly Gly Gly
```

```
                115                 120                 125
Gly Ser Gly Gly Gly Ser Gly Gly Gly Ser Glu Ile Val Leu
        130                 135                 140

Thr Gln Ser Pro Ser Ser Leu Ser Ala Ser Leu Gly Glu Ser Val Thr
145                 150                 155                 160

Leu Ala Cys Arg Gly Ala Ser Gln Asp Ile Gly Gly Arg Leu Asn Trp
                165                 170                 175

Leu Gln Gln Glu Ala Asp Gly Thr Ile Lys Arg Leu Ile Tyr Ala Thr
            180                 185                 190

Ser Ser Leu Asp Ser Gly Val Pro Lys Arg Phe Ser Gly Ser Arg Ser
        195                 200                 205

Gly Ser Asp Tyr Ser Leu Thr Ile Ser Ser Leu Glu Ser Glu Asp Phe
    210                 215                 220

Val Asp Tyr Tyr Cys Leu Gln Tyr Asp Arg Ser Pro Tyr Thr Phe Gly
225                 230                 235                 240

Gly Gly Thr Lys Leu Glu Ile Lys Arg Gly Asp Ala Ala Pro Thr Val
                245                 250                 255

Ala Ala

<210> SEQ ID NO 10
<211> LENGTH: 24
<212> TYPE: DNA
<213> ORGANISM: Artificial Sequence
<220> FEATURE:
<223> OTHER INFORMATION: HC bw primer
<220> FEATURE:
<221> NAME/KEY: misc_feature
<222> LOCATION: (19)..(19)
<223> OTHER INFORMATION: n is a, c, g, or t

<400> SEQUENCE: 10
aggggccagt ggatagacng atgg                                          24

<210> SEQ ID NO 11
<211> LENGTH: 33
<212> TYPE: DNA
<213> ORGANISM: Artificial Sequence
<220> FEATURE:
<223> OTHER INFORMATION: LC bw primer

<400> SEQUENCE: 11
acctgcggcc gctacagttg gtgcagcatc agc                                33

<210> SEQ ID NO 12
<211> LENGTH: 38
<212> TYPE: DNA
<213> ORGANISM: Artificial Sequence
<220> FEATURE:
<223> OTHER INFORMATION: MHV78 fw primer 1

<400> SEQUENCE: 12
gcggcccagc cggccsaggt ccagcagctg cagyytgg                           38

<210> SEQ ID NO 13
<211> LENGTH: 38
<212> TYPE: DNA
<213> ORGANISM: Artificial Sequence
<220> FEATURE:
<223> OTHER INFORMATION: MHV78 fw primer 2

<400> SEQUENCE: 13
gcggcccagc cggcccaggt rcagctgaag sagtcagg                           38
```

<210> SEQ ID NO 14
<211> LENGTH: 38
<212> TYPE: DNA
<213> ORGANISM: Artificial Sequence
<220> FEATURE:
<223> OTHER INFORMATION: MHV78 fw primer 3

<400> SEQUENCE: 14
gcggcccagc cggccgakgt gcagcttcag cagtcrgg                              38

<210> SEQ ID NO 15
<211> LENGTH: 38
<212> TYPE: DNA
<213> ORGANISM: Artificial Sequence
<220> FEATURE:
<223> OTHER INFORMATION: MHV78 fw primer 4

<400> SEQUENCE: 15
gcggcccagc cggccgavgt gawgctggtg gagtctgr                              38

<210> SEQ ID NO 16
<211> LENGTH: 38
<212> TYPE: DNA
<213> ORGANISM: Artificial Sequence
<220> FEATURE:
<223> OTHER INFORMATION: MHV78 fw primer 5

<400> SEQUENCE: 16
gcggcccagc cggccgaagt gcagctgttg gagactgg 38

<210> SEQ ID NO 17
<211> LENGTH: 38
<212> TYPE: DNA
<213> ORGANISM: Artificial Sequence
<220> FEATURE:
<223> OTHER INFORMATION: MHV78 fw primer 6

<400> SEQUENCE: 17
gcggcccagc cggccgaggt tvagvtgcag cagtctgk 38

<210> SEQ ID NO 18
<211> LENGTH: 38
<212> TYPE: DNA
<213> ORGANISM: Artificial Sequence
<220> FEATURE:
<223> OTHER INFORMATION: MHV78 fw primer 7

<400> SEQUENCE: 18
gcggcccagc cggcccaggt tcacctacaa cagtctgg 38

<210> SEQ ID NO 19
<211> LENGTH: 42
<212> TYPE: DNA
<213> ORGANISM: Artificial Sequence
<220> FEATURE:
<223> OTHER INFORMATION: MKV75 fw primer 1

<400> SEQUENCE: 19
ctctggcggt ggcggatcgg atgytktkvt gacccaaact cc 42

<210> SEQ ID NO 20
<211> LENGTH: 42
<212> TYPE: DNA
<213> ORGANISM: Artificial Sequence
<220> FEATURE:

<223> OTHER INFORMATION: MKV75 fw primer 2

<400> SEQUENCE: 20
ctctggcggt ggcggatcgr acattgtgct gacmcaatct cc                42

<210> SEQ ID NO 21
<211> LENGTH: 42
<212> TYPE: DNA
<213> ORGANISM: Artificial Sequence
<220> FEATURE:
<223> OTHER INFORMATION: MKV75 fw primer 3

<400> SEQUENCE: 21
ctctggcggt ggcggatcgs aaawtgtkct cwcccagtct cc                42

<210> SEQ ID NO 22
<211> LENGTH: 42
<212> TYPE: DNA
<213> ORGANISM: Artificial Sequence
<220> FEATURE:
<223> OTHER INFORMATION: MKV75 fw primer 4

<400> SEQUENCE: 22
ctctggcggt ggcggatcgs aaawtctkct cwcccagtct cc                42

<210> SEQ ID NO 23
<211> LENGTH: 42
<212> TYPE: DNA
<213> ORGANISM: Artificial Sequence
<220> FEATURE:
<223> OTHER INFORMATION: MKV75 fw primer 5

<400> SEQUENCE: 23
ctctggcggt ggcggatcgs aaawtttkct cwcccagtct cc                42

<210> SEQ ID NO 24
<211> LENGTH: 42
<212> TYPE: DNA
<213> ORGANISM: Artificial Sequence
<220> FEATURE:
<223> OTHER INFORMATION: MKV75 fw primer 6

<400> SEQUENCE: 24
ctctggcggt ggcggatcga rcattgtgat gacccagwct ca                42

<210> SEQ ID NO 25
<211> LENGTH: 42
<212> TYPE: DNA
<213> ORGANISM: Artificial Sequence
<220> FEATURE:
<223> OTHER INFORMATION: MKV75 fw primer 7

<400> SEQUENCE: 25
ctctggcggt ggcggatcga rcattgtgat gacccagwct cc                42

<210> SEQ ID NO 26
<211> LENGTH: 42
<212> TYPE: DNA
<213> ORGANISM: Artificial Sequence
<220> FEATURE:
<223> OTHER INFORMATION: MKV75 fw primer 8

<400> SEQUENCE: 26
ctctggcggt ggcggatcgg rcattgtgat gacccagwct ca                42

```
<210> SEQ ID NO 27
<211> LENGTH: 42
<212> TYPE: DNA
<213> ORGANISM: Artificial Sequence
<220> FEATURE:
<223> OTHER INFORMATION: MKV75 fw primer 9

<400> SEQUENCE: 27
ctctggcggt ggcggatcgg rcattgtgat gacccagwct cc                          42

<210> SEQ ID NO 28
<211> LENGTH: 42
<212> TYPE: DNA
<213> ORGANISM: Artificial Sequence
<220> FEATURE:
<223> OTHER INFORMATION: MKV75 fw primer 10

<400> SEQUENCE: 28
ctctggcggt ggcggatcgg atatccagat gacacagact ac                          42

<210> SEQ ID NO 29
<211> LENGTH: 42
<212> TYPE: DNA
<213> ORGANISM: Artificial Sequence
<220> FEATURE:
<223> OTHER INFORMATION: MKV75 fw primer 11

<400> SEQUENCE: 29
ctctggcggt ggcggatcgg amatcmwgat gacccartct cc                          42

<210> SEQ ID NO 30
<211> LENGTH: 63
<212> TYPE: DNA
<213> ORGANISM: Artificial Sequence
<220> FEATURE:
<223> OTHER INFORMATION: linker DNA

<400> SEQUENCE: 30
cgatccgcca ccgccagagc cacctccgcc tgaaccgcct ccaccagggg ccagtggata       60
gac                                                                     63

<210> SEQ ID NO 31
<211> LENGTH: 24
<212> TYPE: DNA
<213> ORGANISM: Artificial Sequence
<220> FEATURE:
<223> OTHER INFORMATION: Seq primer 1

<400> SEQUENCE: 31
caacgtgaaa aaattattat tcgc                                              24

<210> SEQ ID NO 32
<211> LENGTH: 23
<212> TYPE: DNA
<213> ORGANISM: Artificial Sequence
<220> FEATURE:
<223> OTHER INFORMATION: Seq primer 6

<400> SEQUENCE: 32
catttactta aaagacatac tcc                                               23
```